United States Patent
Mateu et al.

(10) Patent No.: US 10,138,374 B2
(45) Date of Patent: Nov. 27, 2018

(54) LOW ENERGY, COLD PROCESS FORMULATION AID

(71) Applicants: Juan R. Mateu, Oak Ridge, NJ (US); Adam Perle, Fairfield, NJ (US)

(72) Inventors: Juan R. Mateu, Oak Ridge, NJ (US); Adam Perle, Fairfield, NJ (US)

(73) Assignee: Jeen International Corp., Fairfield, NJ (US)

( * ) Notice: Subject to any disclaimer, the term of this patent is extended or adjusted under 35 U.S.C. 154(b) by 0 days.

(21) Appl. No.: 14/276,404

(22) Filed: May 13, 2014

(65) Prior Publication Data

US 2014/0336308 A1     Nov. 13, 2014

Related U.S. Application Data

(63) Continuation-in-part of application No. 13/630,863, filed on Sep. 28, 2012, now abandoned, which is a continuation of application No. 13/082,317, filed on Apr. 7, 2011, now Pat. No. 8,299,162.

(60) Provisional application No. 61/321,765, filed on Apr. 7, 2010, provisional application No. 61/347,664, filed on May 24, 2010, provisional application No. 61/435,128, filed on Jan. 21, 2011.

(51) Int. Cl.
| | |
|---|---|
| *C08L 91/06* | (2006.01) |
| *A61K 8/31* | (2006.01) |
| *A61K 8/37* | (2006.01) |
| *A61Q 17/00* | (2006.01) |
| *A61K 8/81* | (2006.01) |
| *A61K 8/92* | (2006.01) |
| *A61K 8/39* | (2006.01) |

(52) U.S. Cl.
CPC .......... *C08L 91/06* (2013.01); *A61K 8/31* (2013.01); *A61K 8/375* (2013.01); *A61K 8/39* (2013.01); *A61K 8/8111* (2013.01); *A61K 8/922* (2013.01); *A61Q 17/00* (2013.01); *A61K 2800/10* (2013.01); *C08L 2205/02* (2013.01)

(58) Field of Classification Search
CPC ..... C08L 91/06; C08L 33/08; A61K 2800/10; A61K 8/31; A61K 8/375
See application file for complete search history.

(56) References Cited

U.S. PATENT DOCUMENTS

| | | | | | |
|---|---|---|---|---|---|
| 4,566,980 | A | * | 1/1986 | Smith | C11D 17/0039 510/101 |
| 5,534,265 | A | * | 7/1996 | Fowler | A61K 8/042 424/401 |
| 5,700,516 | A | * | 12/1997 | Sandvick | C08L 91/06 162/189 |
| 6,132,739 | A | * | 10/2000 | Leverett | A61K 8/044 424/401 |
| 8,299,162 | B2 | * | 10/2012 | Mateu | A61K 8/042 424/401 |
| 2004/0120918 | A1 | * | 6/2004 | Lintner | A61K 8/64 424/70.14 |
| 2004/0180021 | A1 | * | 9/2004 | De La Poterie | A61K 8/731 424/70.12 |

FOREIGN PATENT DOCUMENTS

GB          993794     *   6/1965

OTHER PUBLICATIONS

TRS data on Syntran 5760, pp. 1-2, accessed on Aug. 25, 2014, http://www.interpolymer.com/stuff/contentmgr/files/dd732d26ebafa0517c36b4c4144c93d5/miscdocs/syntran_5760_trs_letterhead_010405.pdf).*

* cited by examiner

*Primary Examiner* — Alma Pipic
(74) *Attorney, Agent, or Firm* — Louis C. Paul

(57) ABSTRACT

Provided are cold process formulation aids (CPFAs), methods for their manufacture, and personal care products made using them. CPFAs include (i) a polymer having an aliphatic backbone and a plurality of pendant groups thereon that are pendant ionic or ionizable groups, or pendant groups having at least one permanent dipole that includes an acid, alcohol, thiol, ester, amine, amide, imide, imine, or nitrile moiety, and (ii) a wax selected from natural waxes and synthetic waxes, wherein if the wax is not micronized and is not self-emulsifying, the ratio, by weight, of the non-micronized wax to the polymer having an aliphatic backbone is from about 60:40 to 80:20, and if the wax is a micronized wax or a self-emulsifying wax, the ratio, by weight, of wax to polymer backbone is 70:30 to 98:2.

27 Claims, No Drawings and claims the benefit of priority to, U.S. Non-Provisional application Ser. No. 13/630,863, filed on Sep. 28, 2012. Application Ser. No. 13/630,863 claims the benefit of priority to U.S. Non-Provisional application Ser. No. 13/082,317, filed on Apr. 7, 2011, and now U.S. Pat. No. 8,299,162, claims the priority benefit of U.S. Provisional Application Ser. No. 61/321,765 filed on Apr. 7, 2010, U.S. Provisional Application Ser. No. 61/347,664 filed on May 24, 2010, and U.S. Provisional Application Ser. No. 61/435,128 filed on Jan. 21, 2011. The contents of U.S. Non-Provisional application Ser. Nos. 13/630,863 and 13/082,317, as well as U.S. Provisional Application Ser. Nos. 61/321,765, 61/347,664, and 61/435,128 are each incorporated herein by reference in their entirety.

LOW ENERGY, COLD PROCESS FORMULATION AID

CROSS-REFERENCES TO RELATED APPLICATIONS

This application is a continuation-in-part of,

STATEMENT REGARDING FEDERALLY SPONSORED RESEARCH OR DEVELOPMENT

Not applicable.

FIELD OF THE INVENTION

The present invention is directed to low-energy, low carbon footprint, cold process formulation aids (CPFAs), methods for their manufacture, and methods of using them in the manufacture of personal care products. When one or a combination of CPFAs of the present invention is/are combined with an aqueous medium and other ingredients, an emulsion (or hydrogel) can be formed, often at temperatures not exceeding 30° C.

BACKGROUND OF THE INVENTION

CPFAs of the present invention allow the creation of stable emulsions and hydrogels in a manner that is markedly more efficient than the conventional manufacturing processes in several respects. Conventional emulsion manufacturing processes requires two heated mixing vessels. The aqueous phase is weighed, staged and introduced into a first vessel. The oil phase is weighed, staged and introduced into a second vessel. Prior to being combined, the contents of the two separate vessels must each be heated to a temperature greater than the melt point of the highest wax in the emulsion, typically by 5 degrees Centigrade. If, for example, the aqueous phase is colder than the oil phase, waxes in the oil phase can crystallize. Further, in conventional emulsion manufacturing—particularly, complex multi-ingredient formulations—ingredients must be carefully weighed, added in specific order, and mixed for specific mixing times. Addition of one phase into another phase is often sensitive to the rate of addition. If two phases are combined too quickly, increased mixing time, and energy, is required to stabilize the emulsion.

Using CPFAs of the present invention is simpler and requires less energy. CPFAs of the present invention allow the two phases of the emulsion, aqueous and oil, to be combined into a single vessel, not two (or more) vessel, and thereafter mixed and heated to the desired temperature. Only one vessel needs to be heated (and cleaned). At low as well as high temperatures, the mixture containing CPFA is emulsified and homogenous. Moreover, crystallization of waxes does not occur when manufacturing emulsions (or hydrogels) using CPFAs of the present invention.

Importantly, in conventional manufacturing processes, the emulsion is not stabilized until the emulsion is cooled down. This "cool down" stage is critical. However, the rate and duration of cool down can impact the sensorial properties of the final finished product, often causing batch-to-batch variation. CPFAs of the present invention solve this problem, providing a streamlined process, with fewer addition steps, using only one vessel, with significantly lower energy requirements to create reproducible emulsions (and hydrogels).

Polyacrylic acids, polyacrylates, polycacrylate copolymers, polyacrylate crosspolymers, and their respective salts (collectively referred to in the present application as "Polyacrylic Acid Derivatives" and abbreviated as "PADs")—components of the CPFAs of the present invention—are typically provided by suppliers of chemical raw materials in powder form and serve a number of functions in personal care formulations (as well as in paints and other surface coatings, adhesives, and textiles), including as aqueous rheology modifiers. However, when provided in powder form, PADs are not easily or thoroughly dispersed, and often form aggregates. To overcome these limitations, PADs are commonly sold as dispersions in a solvent also containing an emulsifier. When provided in the form of a dispersion, the powder is "plasticized", and is thus more easily added to an emulsion to achieve the desired rheology. Typically, the solvent is petroleum derived (e.g., mineral oil or a hydrogenated alkene, such as polydecene, polybutylene, or squalene) and the emulsifier is ethoxylated. There is, however, a growing demand to reduce the use of petroleum derived ingredients, especially in personal care formulations. Accordingly, there is a need for being able to disperse PADs without petroleum-derived solvents and without forming aggregates. This need is met by the inventive compositions of the present invention. In personal care formulations, esters are among the most common ingredients—functioning as emollients and conditioners (e.g., Isopropyl Myristate), as solvents (e.g., Ethyl Acetate), as fragrance components (e.g., Methyl Salicylate), and as preservatives (e.g., Propylparaben). Caprylic/Capric Glycerides ("CTG") is also widely used for its emollient properties, increasing the water content of skin by blocking the evaporative loss of water. However, PADs are known to have limited or no solubility in cosmetically acceptable esters or CTG. To the extent PADs could be mixed into such esters or CTG, the resultant sticky paste was very high in viscosity, too high to be used in the manufacture of personal care products. Accordingly, there is a need to be able to render PADs are directly soluble in cosmetically-acceptable esters and CTG, without a petroleum-derived solvent. That need is met by the compositions and methods of the present invention whereby PADs (and mixtures thereof) are combined specific minimum amount of one or a mixture of emulsifying waxes, which, in certain embodiments, are polyglyceryl esters, thereby rendering the PADs directly soluble in cosmetically-acceptable esters and CTG.

SUMMARY OF THE INVENTION

The present invention relates to cold process formulation aids (CPFAs), methods for their manufacture, uses of CPFAs in making cold process emulsions and hydrogels for use in personal care, household and industrial applications. The cold processing aids include at least one wax and a polymer having a backbone and a plurality of pendant groups thereon that are pendant ionic or ionizable groups, or pendant groups having at least one permanent dipole that includes an acid, alcohol, thiol, ester, amine, amide, imide, imine, or nitrile moiety. The backbone can be an aliphatic backbone or a polysaccharide backbone, a siloxane backbone, or a polyamide backbone. The present invention is also directed to compositions and methods for rendering polyacrylic acids, polyacrylates, polyacrylate copolymers, polyacrylate crosspolymers, and their respective salts directly soluble in cosmetically-acceptable esters and CTG by combining, in specific ratios, the PAD with an emulsifying wax, which, in preferred embodiments is a polyglyceryl ester.

DETAILED DESCRIPTION OF THE INVENTION

As used in herein, the term "emulsion" is to be understood as a homogenous mixture of at least two otherwise immiscible ingredients. Emulsions can be of the oil-in-water type or the silicone-in-water type, or, in certain embodiments, so-called "invert" emulsions, of the water-in-oil type, the silicone-in-water type. Additionally, so-called "triple" emulsions—including, for example, water-in-oil-in-water, can be made by combining the cold process aid of the present invention with an aqueous medium as well as other ingredients.

As used herein, "aqueous medium" refers to a substance that is preferably liquid at room temperature (22°-27° C.) but does not exclude the use of said liquid at a temperature lower than the melt point of the patentable compositions described in this invention and that includes at least 50%, preferably at least 75%, still more preferably at least 90%, by weight, water. The remainder of the aqueous medium can be compounds that are freely miscible with water, for example alcohols such as ethanol and the propanols, and polyalkylene glycols, to mention just a few.

The adjective "cold" in the term "cold process"—used in the present application to describe "cold process formulation aid" as well as a method for creating emulsions or hydrogels using such a formulation aid—means a temperature below the melting point of the at least one wax that is an integral component of the cold process formulation aid. Accordingly, when a formulator adds a cold process formulation aid of the present invention to an aqueous medium, an emulsion or hydrogel is formed without having to heat the aqueous medium above the melting point of the at least one wax. This "one wax" will be the wax in the CFPA that has the highest melt point.

As used herein, "cosmetically-acceptable ester" refers to a compound formed by the reaction of a mono-, di- or tri-carboxylic acid with an aliphatic or aromatic alcohol resulting in, respectively, monoesters, diesters and triesters, each as defined below. The carboxylic acid may contain from 2 to 30 carbon atoms, and may be straight-chain or branched-chain, saturated or unsaturated. The carboxylic acid may also be substituted with one or more hydroxyl groups. The aliphatic or aromatic alcohol may contain 2 to 30 carbon atoms, may be straight-chain or branched-chain, saturated or unsaturated. The aliphatic or aromatic alcohol may contain one or more substituents including, for example, a hydroxyl group. The ester is "cosmetically-acceptable" such that it is not irritating or sensitizing when applied to the skin As used in the present invention, "cosmetically-acceptable monoesters" are esters formed by the reaction of a monocarboxylic acid having the formula R—COOH, wherein R is a straight or branched chain saturated or unsaturated alkyl having 2 to 30 carbon atoms, or phenyl; and an alcohol having the formula R—OH wherein R is a straight or branched chain saturated or unsaturated alkyl having 2-30 carbon atoms, or phenyl. Either one or both of the acid or alcohol may be a "fatty" acid or alcohol, having from about 6 to 22 carbon atoms.

As used herein, "cosmetically-acceptable diesters" refer to the reaction products of a dicarboxylic acid and an aliphatic or aromatic alcohol. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. The aliphatic or aromatic alcohol may be substituted with one or more substitutents such as hydroxyl. Preferably, one or more of the acid or alcohol is a fatty acid or alcohol containing 14-22 carbon atoms. The dicarboxylic acid may also be an alpha hydroxy acid.

"Cosmetically-acceptable triesters" as used in the present application refers to the reaction products of a tricarboxylic acid and an aliphatic or aromatic alcohol The acid and alcohol contain 2 to 30 carbon atoms, and may be saturated or unsaturated, straight or branched chain, and, may be substituted with one or more hydroxyl groups. Preferably, one or more of the acid or alcohol is a fatty acid or alcohol containing 14 to 22 carbon atoms.

In describing the weight of ingredients used in forming the compositions of the present invention, the word "about" is to be understood to refer to that variation in the measured quantity as would be expected by one skilled in the art exercising a level of care commensurate with the objective of the measurement and the equipment used, and includes uncertainties that may be introduced by mathematical rounding errors. Unless otherwise expressly noted or required by the context, all percentages refer to percentages by weight (wt-%) and the percentage of an ingredient is the percentage by weight of the ingredient by weight of the composition/blend in which the ingredient is a component. For example, in a blend or mixture described as containing ingredient X at a concentration of 2%, ingredient X would constitute 2% weight of the blend. In a first aspect of the present invention, one or more CPFAs are added to an aqueous medium at temperatures greater than the melt point of the CPFA, or in the case of more than one CPFA the highest melt point of the CPFAs.

In embodiments of this first aspect of the invention, the cold process formulation aid of the present invention, in certain of its embodiments, includes a polymer having an aliphatic backbone and a plurality of pendant groups thereon that are pendant ionic or ionizable groups, and/or that are pendant groups having at least one permanent dipole that includes an acid, alcohol, thiol, ester, amines, amide, imide, imine, or nitrile moiety.

By aliphatic backbone is meant that the main polymer chain consists of a majority, preferably essentially exclusively, of carbon-carbon bonds.

Polymers having an aliphatic backbone are well known in the polymer arts and can be made by, for example, free-radical initiated polymerization of compounds (monomers) having a carbon-carbon double bond, colloquially referred to as "vinyl-type monomers". Poly(methyl methacrylate) and poly(acrylic acid) are examples of polymers having aliphatic backbones that can be obtained by the free-radical polymerization of, respectively, methyl methacrylate and acrylic acid.

The polymers having an aliphatic backbone and a plurality of pendant groups thereon that are pendant ionic or ionizable groups, and/or that are pendant groups having at least one permanent dipole that includes an acid, alcohol, thiol, ester, amine, amide, imide, imine, or nitrile moiety useful in making the cold process formulation aid of the present invention can be homopolymers, obtained by polymerizing a single monomer, or they can be co- or ter-polymers, obtained by polymerizing a mixture of two or three monomers.

The polymers having an aliphatic backbone and a plurality of pendant groups can be, and in certain embodiments are, crosslinked polymers. Crosslinking can be achieved by methods known in the art, for example by combining a compound ("crosslinking agent") having two or more polymerizable carbon-carbon double bonds with the monomer(s) being polymerized. Allyl ether and α,ω-diallyl ethers and α,ω-diacrylate or dimethacrylate esters of poly(alkylene glycols) are examples of crosslinking agents that can be used to prepare crosslinked polymers having an aliphatic backbone and a plurality of ionic, ionizable, or permanent dipole-containing pendant groups. Others crosslinking agents are known in the art.

The pendant groups, occasionally referred to in the art as "side-chains", useful in the practice of certain embodiments of the present invention are groups, or "radicals", that are attached to a carbon atom in the main polymer chain by a chemical bond, but are not part of the main polymer chain. The pendant groups attached to the main polymer chain can be present in the monomer(s) at the time of polymerization, or they can be formed by post-polymerization reaction, for example post-polymerization salification or hydrolysis of a salifiable or hydrolysable functional group that was present as, or as part of, a substituent on the monomer(s) at the time of polymerization. The methoxycarbonyl [—C(O)—OCH$_3$] group of poly(methyl methacrylate), obtained by polymerization of methyl methacrylate, is an example of a pendant group that was present as a substituent on a monomer at the time of polymerization.

The pendant groups of the polymers having an aliphatic backbone and a plurality of pendant groups that are useful in the practice of certain embodiments of the present invention can be ionic or ionizable, or they can be groups that have at least one permanent dipole due to the presence in the pendant group of an acid, alcohol, thiol, ester, amine, amide, imide, imine, or nitrile moiety, or they can be a combination of any of the foregoing.

Ionic pendant groups carry permanent ionic charges. The carboxylate group, —C(O)O$^-$M$^+$, where M$^+$ is a metal cation, especially a cation of an alkali metal, is an example of an ionic pendant group. Sodium polyacrylate (the sodium salt of poly(acrylic acid)) is a preferred polymer having an aliphatic backbone and a plurality of pendant ionic groups for use in certain embodiments of the cold process formulation aid of the present invention. Other polycacrylate copolymers, polyacrylate crosspolymers, and their respective salts may be used in forming CPFAs (as well as in other aspects of the present invention as further described below).

Poly(acrylic acid), also referred to in the present application as poly(acrylic) acid, is the polymer of acrylic acid (2-propenoic acid) and conforms generally to the formula:

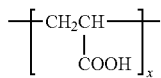

Poly(acrylic acid) is soluble in tetrahydrofuran, water, methanol, and ethanol, but precipitates from ether, acetone, and hexane, and is commercially available under the following tradenames: AC-10H—Nihon Junyaku Company, Ltd. (Tokyo, Japan); Creagel TN 500—C.I.T. sarl (Dreux, France); Jurymer AC-10LHP—Nihon Junyaku Company, Ltd. (Tokyo, Japan); Modarez V 1300 PX—Synthron (Levallois, France); OriStar PALA—Orient Stars LLC (Torrance, Calif.).

The term "Polyacrylate" as used in the present application refers to a synthetic resins produced by the polymerization of acrylic esters. The term "acrylic ester" is well-known to the person having ordinary skill in the chemical arts. Acrylic acid molecules are esterified by reaction with alcohols, most commonly ethanol or methanol. In the esterification reaction, the hydrogen atom in the carboxyl group on the acrylic acid molecule is replaced by an organic group—a methyl group in reactions with methanol, and an ethyl group in reactions with ethanol. The most common polyacrylates are polyethyl acrylate and polymethyl acrylate, represented by the formula CH$_2$=CHCO$_2$R, where R is an organic group.

The following is a non-limiting list of polyacrylate salts and their derivatives, which can be used in forming the inventive compositions of the present invention—namely CPFAs as well as blends with glyceryl esters that can be added directly to, and will be directly soluble in, a cosmetically-acceptable ester or CTG.

Sodium Polyacrylate is the sodium salt of Polyacrylic Acid. It is commercially available under the following tradenames: Activsoft MS 100—Innospec Performance Chemicals (Salisbury, N.C.); Acusol AD-7 Polymer—The Dow Chemical Company (Midland, Mich.); Aronvis—Nihon Junyaku Company, Ltd. (Tokyo, Japan); Cosmedia SP—BASF Personal Care and Nutrition Gmbh (Germany); Covacryl AC—Sensient Cosmetic Technologies (France); Covacryl J22—Sensient Cosmetic Technologies (France); Covacryl MV60—Sensient Cosmetic Technologies (France); Covacryl RH—Sensient Cosmetic Technologies (France); Flocare CGEL 100—SNF SAS (Andrezieux, France); Flocare DP/PSD 100—SNF SAS (Andrezieux, France); Flocare G300—SNF SAS (Andrezieux, France); Flocare G800—SNF SAS (Andrezieux, France); RapiThix A-100—Ashland Inc. (Wilmington, Del.); Rheogic 250H—Nihon Junyaku Company, Ltd. (Tokyo, Japan); Rheosol AP—Rheolabs Inc. (South Holland, Ill.); Rhesperse RM100—Innospec Performance Chemicals (Salisbury, N.C.); Sanfresh ST-500-MPSA—Risera Co., Ltd. (Hakodate, Japan);

Ammonium Polyacrylate is the ammonium salt of Polyacrylic Acid and is commercially available under the tradename Covacryl VIP from Sensient Cosmetic Technologies (Saint Ouen L'Aumone, France).

Potassium Polyacrylate is the potassium salt of Polyacrylic Acid.

Potassium Aluminum Polyacrylate is a mixture of the potassium and aluminum salts of Polyacrylic Acid.

Sodium Polyacrylate Starch is a starch grafted with the polymer sodium acrylate. This starch is commercially available under the following tradenames: Makimousse 12—Daito Kasei Kogyo Co., Ltd. (Osaka, Japan); Makimousse 25—Daito Kasei Kogyo Co., Ltd. (Osaka, Japan); Sanfresh ST-100C—Sanyo Chemical Industries Ltd. (Kyoto, Japan); Sanfresh ST-100MC—Sanyo Chemical Industries Ltd. (Kyoto, Japan); Sanwet IM-300MC—Sanyo Chemical Industries Ltd. (Kyoto, Japan)

The term "Acrylates Copolymer" as used in the present application refers to a copolymer of two or more monomers consisting of acrylic acid, methacrylic acid or one of their esters (e.g., polyethyl acrylate and polymethyl acrylate). According to INCI naming conventions, copolymers consisting of two or more constituent monomers are named by listing the monomers separated by a slash (/) followed by the word "Copolymer," e.g., Acrylates/Acrylamide Copolymer. In the case of INCI names assigned to cross polymers before March 2003, the earlier name is retained without copolymer notation. An arbitrary number may follow the name. For example, Polyacrylate-1.

The following is a non-limiting list of Acrylates Copolymers, which can be used to make CPFAs and which, when combined with a glyceryl ester in accordance with the present invention, can be added directly to, and will be directly soluble in, a cosmetically-acceptable ester or CTG.

Polyacrylate-1 is a copolymer of vinyl pyrrolidone, dimethylaminoethyl methacrylate, stearyl acrylate and PPG-3 diacrylate monomers. This copolymer is commercially available under the tradename Cosquat GA467 from Osaka Organic Chemical Ind., LTD. (Osaka, Japan).

Polyacrylate-2 is a copolymer of styrene, acrylamide, octyl acrylate and methyl methacrylate monomers.

Polyacrylate-3 is a copolymer of methacrylic acid, methyl methacrylate, methylstyrene isopropylisocyanate and PEG-40 behenate monomers. This copolymer is commericially available under the tradename Viscophobe DB-1000 from Dow Chemical Company (Midland, Mich.).

Polyacrylate-4 is a polymer of the acrylic monomers having the empirical formula $(C_{24}H_{34}O_{10}.C_{24}H_{22}O_9.C_{24}H_{22}O_9)x$ and is represented by the following structures:

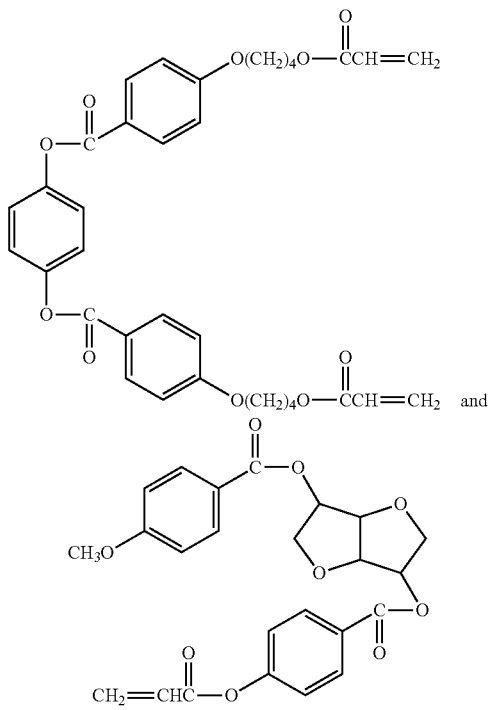

Polyacrylate-5 is a copolymer of styrene, ethylhexyl acrylate, hydroxyethyl acrylate, and one or more monomers of acrylic acid, methacrylic acid, or one of their simple esters.

Polyacrylate-6 is a copolymer of methyl methacrylate, triethoxysilylpropyl-methacrylate, tris(trimethylsiloxy)silylpropylmethacrylate and acryloyloxyethyl (trimethyl)ammonium chloride monomers. This copolymer is commercially available under the tradename MK Polymer from Shin-Etsu Chemical Co. (Tokyo, Japan).

Polyacrylate-7 is a copolymer of 2-acryloylethyl trimethylammonium chloride, acrylic acid, acrylamide, and 2-acrylamido-2-methylpropane sulfonic acid. This copolymer is commercially available under the tradename OF-420 from WSP Chemicals & Technology LLC (Leetsdale, Pa.).

Polyacrylate-8 is a copolymer of hydroxypropylacrylate, butylaminoethyl methacrylate, and one or more monomers of acrylic acid, methacrylic acid, or one of their simple esters. This copolymer is commercially available under the tradename Balance AM from AkzoNobel Global Personal Care (Bridgewater, N.J.).

Polyacrylate-9 is a copolymer of octylpropenamide, butylaminoethyl-methacrylate, hydroxypropylmethacrylate, and one or more momoners of acrylic acid, methacrylic acid or one of thier simple esters. This copolymer is commercially available under the tradename Amphomer 28-4920 from AkzoNobel Global Personal Care (Bridgewater, N.J.).

Polyacrylate-10 is a copolymer of sodium acryloyldimethyltaurate, sodium acrylate, acrylamide and vinyl pyrrolidone monomers.

Polyacrylate-11 is a copolymer of sodium acryloyldimethyl taurate, sodium acrylate, hydroxyethyl acrylate, lauryl acrylate, butyl acrylate and acrylamide monomers.

Polyacrylate-12 is a copolymer of $C_{3-11}$ acrylate, styrene, Methacrylic Acid (q.v.) and acetoacetoxyethyl methacrylate monomers. This copolymer is commercially available under the tradename Acudyne NP-1 from Dow Chemical Company (Midland, Mich.).

Polyacrylate-13 is the copolymer of acrylic acid, acrylamide, sodium acrylate and sodium acryloyldimethyltaurate monomers.

Polyacrylate-14 is a copolymer of PEG-25 $C_{10-30}$ alkyl ether methacrylate, PEG-20 PPG-5 allyl ether and one or more monomers consisting of acrylic acid, methacrylic acid or one of their simple esters. This copolymer is commercially available under the tradename Fixate PLUS Polymer from Lubrizol Advanced Materials, Inc. (Cleveland, Ohio).

Polyacrylate-15 is a copolymer of n-butyl acrylate, ethyl acrylate, methyl methacrylate, ethylene, methacrylic acid and styrene monomers. This copolymer is commercially available under the tradename Syntran PC 5208 from Interpolymer Corporation (Canton, Mass.).

Polyacrylate-16 is a copolymer of n-butyl acrylate, diethylaminoethyl methacrylate, ethyl acrylate, methacrylic acid, hydroxypropyl methacrylate, methyl methacrylate and styrene monomers. This copolymer is commercially available under the tradename Syntran PC5112 from Interpolymer Corporation (Canton, Mass.).

Polyacrylate-17 is a copolymer of n-butyl acrylate, diethylaminoethyl methacrylate, hydroxyethyl methacrylate, methyl methacrylate and t-butylaminoethyl methacrylate.

Polyacrylate-18 is a copolymer of n-butyl acrylate, ethyl acrylate, methacrylic acid, hydroxypropyl methacrylate and styrene monomers.

Polyacrylate-19 is a copolymer of n-butyl acrylate, methacrylic acid, methyl methacrylate, dimethylaminoethyl methacrylate and methoxy PEG-8 acrylate.

Polyacrylate-20 (also known as Acrylates/Methoxy PEG-10 Maleate/Styrene Copolymer) is a copolymer of styrene, methoxy PEG-10 maleate and one or more monomers consisting of acrylic acid, methacrylic acid or one of their simple esters. Polyacrylate-20 is commercially available as Opulyn 305 Opacifier from The Dow Chemical Company (Midland, Mich.).

Polyacrylate-21 is a copolymer of 2-ethylhexyl acrylate, butyl methacrylate, methacrylic acid, methyl methacrylate, hydroxypropyl methacrylate and styrene.

Polyacrylate-22 is a complex polymer that is prepared by first reacting isophorone diisocyanate (IPDI with a copolymer made from Adipic Acid (q.v.) and Neopentyl Glycol (q.v.). The isocyanate groups on the resulting polymer are then reacted with hydroxyethyl methacrylate followed by quenching with ethanol to eliminate residual urethane groups. Finally, the polymer above is copolymerized with acrylic acid, methacrylic acid, and methyl methacrylate, then partially neutralized with aminomethyl propanol (AMP). This polymer is commercially available under the tradename Luviset Shape from BASF Corporation (Florham Park, N.J.).

Polyacrylate-24 is a copolymer of Dimethylaminoethyl Methacrylate (q.v.), Lauryl Methacrylate (q.v.), stearyl methacrylate and Methyl Methacrylate (q.v.) monomers modified with hydrogen peroxide.

Polyacrylate-25 is a copolymer of Dimethylaminoethyl Methacrylate (q.v.), Lauryl Methacrylate (q.v.), stearyl methacrylate, Methyl Methacrylate (q.v.) and Butyl Methacrylate (q.v.), modified with hydrogen peroxide.

Polyacrylate-26 is a copolymer of n-butyl acrylate, t-butylamino-ethylmethacrylate, methylmethacrylate, dimethylaminoethyl methacrylate and hydroxyethyl methacrylate monomers.

Polyacrylate-27 is a copolymer of vintyl toluene, 2-ethylhexyl acrylate, 2-hydroxyethyl methacrylate, vinyl imidazole, and methoxy PEG-8 methacrylate monomers. This copolymer is commercially available under the tradename Tinocare WRP from BASF Corporation (Florham Park, N.J.).

Polyacrylate-28 is a copolymer of hydroxyethyl acrylate, sodium acryloyldimethyltaurate, sodium acrylate and tris(hydroxymethyl)-acrylamidomethane. This copolymer is commercially available under the tradename Sepinov F900 from Seppic (Paris, France).

Polyacrylate-29 is a copolymer of stearyl methacrylate, methoxy PEG-9 methacrylate and methacrylic acid.

Polyacrylate-30 is a copolymer of acrylonitrile, methacrylic acid, octyl acrylate, and styrene.

Polyacrylate-31 is a copolymer of $C_{1-18}$ alkyl acrylate, $C_{1-8}$ alkyl acrylate, methoxymethyl acrylamide and one or more monomers consisting of acrylic acid, methacrylic acid or one of their simple esters neutralized with aminomethylpropanol (AMP). This copolymer is commercially available under the tradename Plascize L-9959 from Goo Chemical Company, Ltd. (Kyoto, Japan).

Polyacrylate-32 is a copolymer of PEG/PPG-23/6 Dimethicone (q.v.), sodium acryloyldimethyltaurate, citraconic anhydride and one or more monomers of acrylic acid, methacrylic acid or one of their simple esters. This copolymer is commercially available under the tradename Fixate Design Polymer from Lubrizol Advanced Materials, Inc. (Cleveland, Ohio).

Polyacrylate-33 is a copolymer that conforms generally to the formula (structure below) where R represents a $C_{16-22}$ alkyl group.

or more monomers of acrylic acid, methacrylic acid or one of their simple esters neutralized with aminomethylpropanol.

Dimethicone PEG-8 Polyacrylate is the siloxane polymer obtained by free radical polymerization of PEG-8 Dimethicone (q.v.) esterified with acrylic acid. This polymer is commercially available under the tradename Silsoft Surface PF from Momentive Performance Materials (Friendly, W. Va.).

The term "Acrylates Crosspolymer" as used in the present application refers to a copolymer of acrylic acid, methacrylic acid or one of its esters, crosslinked with glycol dimethacrylate.

Under INCI nomenclature conventions, crosspolymers consisting of two or more constituent monomers are named by listing the monomers separated by a slash (/) followed by the word "Crosspolymer". In the case of INCI names assigned to cross polymers before March 2003, the earlier name is retained without copolymer notation. An arbitrary number may follow the name. For example, Polyacrylate-1 Crosspolymer.

The following is a non-limiting list of Acrylates Crosspolymers, which can be used to form a CPFA of the present invention, and when combined with a glyceryl ester in accordance with the present invention, can be added directly to, and will be directly soluble in, a cosmetically-acceptable ester or CTG.

Polyacrylate-1 Crosspolymer is a copolymer of one or more simple esters of acrylic or methacrylic acid, $C_{1-4}$ dialkylamino $C_{1-6}$ alkyl methacrylate, PEG/PPG-30/5 allyl ether, PEG 20-25 $C_{10-30}$ alkyl ether methacrylate, hydroxy $C_{2-6}$ alkyl methacrylate crosslinked with ethylene glycol

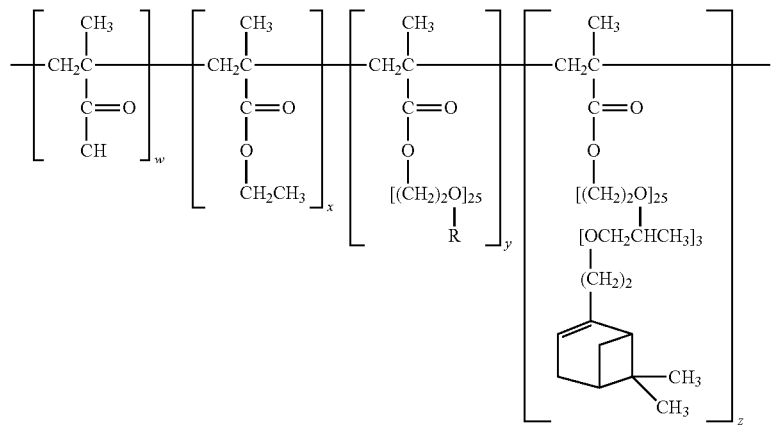

Polyacrylate-33 is commercially available under the tradename Rheomer 33 from Rhodia Novecare (Bristol, Pa.).

Polyacrylate-34 is a copolymer of octoxy PEG-8 PPG-6 methacrylate, PPG-9 methacrylate, PPG-6 acrylate and 2-methoxyethylacrylate monomers.

Polyacrylate-35 is formed by reacting Dipentaerythrityl Pentaacrylate (q.v.) with the cyclic trimer of hexamethylene diisocyanate.

Polyacrylate-36 is a copolymer of Butyl Methacrylate (q.v.), HEMA (q.v.), PEG-10 acrylate, PPG-6 acrylate, and dimethylacrylamide.

Polyacrylate-37 is a copolymer of perfluorohexylethyl acrylate, PEG-5 metha-crylate, acrylic acid and phosphonoxyethyl methacrylate. This copolymer is commercially available under the tradename FPL from Daito Kasei Kogyo Co., Ltd. (Osaka, Japan).

AMP-Acrylates Polyacrylate Crosspolymer-9 is a polymer of hydroxyethylacrylate, methoxyethylacrylate, and one dimethacrylate. This copolymer is commercially available under the tradename Carbopol Aqua CC Polymer from Lubrizol Advanced Materials, Inc. (Cleveland, Ohio).

Polyacrylate-2 Crosspolymer is a copolymer of PEG/PPG-23/6 Dimethicone citraconate, $C_{10-30}$ alkyl PEG-25 methacrylate, and one or more monomers of acrylic acid, methacrylic acid or one of their simple esters, crosslinked with trimethylolpropane PEG-15 triacrylate. This copolymer is commercially available under the tradename Fixate Superhold Polymer from Lubrizol Advanced Materials, Inc. (Cleveland, Ohio).

Polyacrylate Crosspolymer-3 is a copolymer of butyl acrylate, PEG-10 acrylate, PPG-6 acrylate and dimethylacrylamide, crosslinked by PEG-23 Diacrylate. This copolymer is commercially available under the tradename Plascize L-64S from Goo Chemical Company, Ltd. (Kyoto, Japan).

Polyacrylate Crosspolymer-4 is a copolymer of sodium acryloyldimethyltaurate, dimethyl acrylamide, sodium acrylate, acrylic acid and hydroxyethylacrylate crosslinked with methylene bis-propenamide. This copolymer is commercially available under the tradename Sepinov P500 from Seppic (Paris, France).

Polyacrylate Crosspolymer-5 is the crosslinked copolymer that conforms generally to the formula (structure below) where n has an average value of 7.

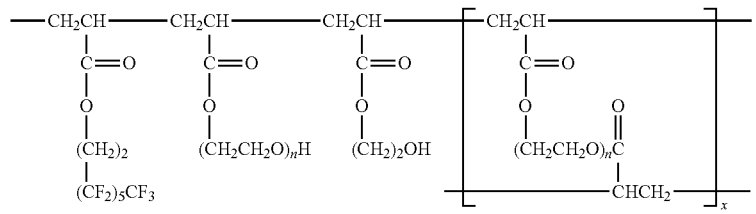

This copolymer is commercially available under the tradename COSP23 from Miyoshi Kasei, Inc. (Urawa, Japan).

Polyacrylate Crosspolymer-6 is a copolymer of ammonium acryloyldimethyl-taurate, dimethylacrylamide, lauryl methacrylate and laureth-4 methacrylate, crosslinked with trimethylolpropane triacrylate. This copolymer is commercially available under the tradename Sepimax Zen from Seppic Affaires Reglementaires (Puteux, France).

Polyacrylate Crosspolymer-7 is a copolymer of methacrylate PPG-6 phosphate and one or more monomers of acrylic acid, methacrylic acid or one of their simple esters, crosslinked with dimethicone PEG/PPG-25/29 acrylate. This copolymer is commercially available under the tradename Y-17552 from Momentive Performance Materials (Friendly, W. Va.).

Polyacrylate Crosspolymer-8 is a copolymer of t-butyl methacrylate, stearyl methacrylate, methoxy PEG-23 methacrylate, and dimethylacrylamide, crosslinked with ethylene glycol dimethacrylate.

Polyacrylate Crosspolymer-9 is a copolymer of t-butylaminoethyl methacrylate and carboxyethyl acrylate, cross-linked with a combination of pentaerythritol tetraacrylate and a hexafunctional acrylate formed by reacting pentaerythritol triacrylate with toluene diisocyanate.

Polyacrylate Crosspolymer-10 is the crosslinked polymer prepared by polymerizing a mixture of trimethoxysilylpropylmethacrylate with trimethyloylpropane trimethacrylate.

Polyacrylate Crosspolymer-11 is a polymer of methacrylic acid, acryloyl dimethyltaurate and dimethylacrylamide, crosslinked with PPG-3 glyceryl triacrylate, and partially neutralized with ammonia. It conforms generally to the structure below.

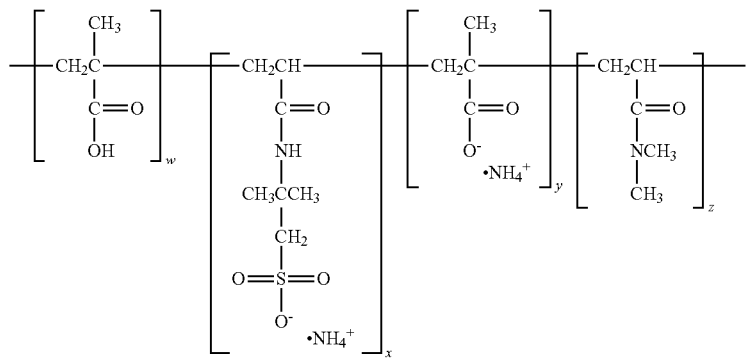

This copolymer is commercially available under the tradename Aristoflex Velvet from Clariant International Ltd. (Muttenz, Switzerland).

Polyacrylate Crosspolymer-12 is a copolymer of t-butyl methacrylate, stearyl methacrylate, methoxy PEG-23 methacrylate, and dimethylacrylamide, crosslinked with methylene bis-acrylamide.

Polyacrylate Crosspolymer-14 is a copolymer of acrylic acid, lauryl methacrylate, cetyl methacrylate, stearyl methacrylate, and phosphorylcholine glycol methacrylate, crosslinked by an allyl ether of pentaerythritol. This copolymer is commercially available under the tradename Phosphomer ST610KC from KCl Ltd. (Seoul, South Korea).

Sodium Polyacrylate Crosspolymer-1 is a complex crosslinked polymer that is made by first preparing a silicone copolymer by reacting a methacrylate-terminated polydimethylsiloxane polymer containing silicon hydride groups with PEG-18/PPG-17 allyl ether. The silicone copolymer is then dispersed in water that contains sodium hydroxide and reacted with Methacrylic Acid (q.v.) and methacryloyl PPG-6 phosphate.

CPFAs of the present invention may also be formed where the polymer having an aliphatic backbone and a plurality of pendant group is an acryloyl ester of a N-dimethyl derivative of taurine. The organic functional group acryloyl (IUPAC prop-2-enoyl) is a univalent radical derived from acrylic acid having the structure CH$_2$=CH—CO—. Taurine (IUPAC 2-aminoethanesulfonic acid) has structural formula NH$_2$CH$_2$CH$_2$SO$_3$H. These compounds are known in the art, and referred to in the present application as acryloyldimethyltaurates.

Additionally, acryloyldimethyltaurates when combined with a glyceryl ester in accordance with the present invention, can be added directly to, and will be directly soluble in, a cosmetically-acceptable ester or CTG.

The following is a non-limiting list of salts, crosspolymers and copolymers of acryloyldimethyltaurate compounds suitable for use in the inventive compositions of the present invention.

Ammonium Polyacryloyldimethyl Taurate is a polymer that conforms generally to the following structure:

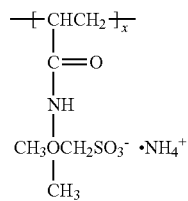

It is commercially available under the tradenames Gransil APK-1, Gransil ORB-25, Gransil ORB-II-JP from Grant Industries, Inc. (Elmwood Park, N.J.) and as SilDerm Formulating Base and SilDerm Formulating Base IF from Active Concepts LLC (Lincolnton, N.C.).

Sodium Polyacryloyldimethyl Taurate is a polymer that conforms generally to the following structure:

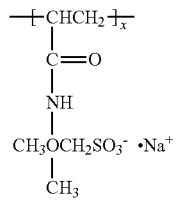

It is commercially available from Seppic (Paris, France) under the tradename Simulgel 800 and as Viscolam AT 100 P from Lamberti S.p.A. (Gallarate, Italy).

Acrylamide/Sodium Acryloyldimethyltaurate/Acrylic Acid Copolymer is a copolymer of acrylamide, sodium acryloyldimethyltaurate and acrylic acid monomers. This copolymer is commercially available under the tradenames Acudyne SCP and Acudyne SCP Hair Styling Hair Fixative Resin from The Dow Chemical Company (Midland, Mich.).

Acrylamide/Sodium Acryloyldimethyltaurate Copolymer is a copolymer of acrylamide and sodium acryloyldimethyltaurate monomers and is available under the tradename Simulgel 600 from Seppic (Paris, France).

Ammonium Acryloyldimethyltaurate/Laureth-7 Methacrylate Copolymer is a copolymer of ammonium acryloyldimethyltaurate and laureth-7 methacrylate monomers.

Ammonium Acryloyldimethyltaurate/Steareth-8 Methacrylate Copolymer is a copolymer of ammonium acryloyldimethyltaurate and steareth-8 methacrylate monomers.

Ammonium Acryloyldimethyltaurate/Vinyl Formamide Copolymer is a copolymer of ammonium acryloyldimethyltaurate and vinyl formamide monomers.

Ammonium Acryloyldimethyltaurate/VP Copolymer is a copolymer of ammonium acryloyldimethyltaurate and vinylpyrrolidone monomers. This copolymer is commercially available under the tradename Aristoflex AVC from Clariant International Ltd. (Muttenz, Switzerland) and also under the tradenames Botanimulse PSF—H and Botanimulse PSF-M from Botanigenics, Inc. (Chatsworth, Calif.).

Hydroxyethyl Acrylate/Sodium Acryloyldimethyl Taurate Copolymer is a copolymer of sodium hydroxyethyl acrylate and acryloyldimethyl taurate monomers and is available from Seppic (Paris, France) under the tradenames Sepiplus S, Sepiplus VG, Simulgel FL, Simulgel I—NS 100, and Simulgel NS.

Sodium Acrylates/Methacryloylethyl Phosphate Copolymer is the sodium salt of a copolymer of acrylic acid, methacrylic acid or one or more of its simple esters and methacryloylethyl phosphate.

Sodium Acrylate/Sodium Acryloyldimethyl Taurate/Acrylamide Copolymer is a copolymer of sodium acrylate, sodium acryloyldimethyltaurate and acrylamide monomers.

Sodium Acrylate/Sodium Acryloyldimethyl Taurate Copolymer is a copolymer of sodium acrylate and sodium acryloyldimethyl taurate monomers. This copolymer is commercially available under the tradename Flocare PSD 30 from SNF SAS (Andrezieux, France) and the tradename Sepinov EG-P from Seppic (Paris, France).

Sodium Acryloyldimethyl Taurate/Acrylamide/VP Copolymer is a copolymer of sodium acryloyldimethyltaurate, acrylamide and vinylpyrrolidone monomers.

Sodium Acryloyldimethyltaurate/Methacrylamidolauric Acid Copolymer is a copolymer of sodium acryloyldimethyltaurate and methyacrylamidolauric acid monomers.

Ammonium Acryloyldimethyltaurate/Beheneth-25 Methacrylate Crosspolymer is a copolymer of ammonium acryloyldimethyltaurate and beheneth-25 methacrylate monomers. This copolymer is commercially available under the tradenames Aristoflex BLV and Aristoflex HMB from Clariant International Ltd. (Muttenz, Switzerland).

Ammonium Acryloyldimethyltaurate/Carboxyethyl Acrylate Crosspolymer is a copolymer of ammonium acryloyl dimethyltaurate and carboxyethyl acrylate crosslinked with trimethylolpropane trimethacrylate. This copolymer is commercially available under the tradename Aristoflex TAC from Clariant International Ltd. (Muttenz, Switzerland).

Ammonium Acryloyldimethyltaurate/Steareth-25 Methacrylate Crosspolymer is a copolymer of ammonium acryloyldimethyltaurate and steareth-25 methacrylate monomers.

Dimethylacrylamide/Sodium Acryloyldimethyltaurate Crosspolymer is a copolymer of dimethylacrylamide and sodium acryloyldimethyltaurate crosslinked with methylene bis-acrylamide. This crosspolymer is commercially available under the tradename SUpolymer G-1 from Toho Chemical Industry Co., Ltd. (Tokyo, Japan).

Melamine/Resorcinol/Acryloyldimethyltaurate/PEG-6 Methacrylate Crosspolymer is a copolymer of melamine, Resorcinol (q.v.), acryloyldimethyltaurate, and PEG-6 methacrylate crosslinked with 1,5-pentanedial.

Sodium Acrylate/Acryloyldimethyltaurate/Dimethylacrylamide Crosspolymer is a crosslinked copolymer of sodium acrylate, acryloyldimethyltaurate and dimethylacrylamide. This crosspolymer is commercially available under the tradename Sepinov P88 from Seppic (Paris, France).

Sodium Acryloyl Dimethyl Taurate/PEG-8 Diacrylate Crosspolymer is a polymer of sodium acryloyl dimethyl taurate crosslinked by PEG-8 diacrylate. This polymer is commercially available under the tradename FW200 Polymer System from Power Paper Ltd. (Petah Tikva, Israel).

Sodium Acryloyldimethyltaurate/VP Crosspolymer is a copolymer of sodium acryloyldimethyltaurate and vinylpyrrolidone crosslinked by 1,1,1-trimethylolpropane triacrylate. This copolymer is commercially available under the tradename Aristoflex AVS from Clariant International Ltd. (Muttenz, Switzerland).

Other copolymers of acrylic acid useful in the practice of the present invention include ammonium VA/acrylates copolymer, sodium acrylates copolymer, ethylene/acrylic acid copolymer, ethylene/calcium acrylate copolymer, ethylene/magnesium acrylate copolymer, ethylene/sodium acrylate copolymer, ethylene/zinc acrylate copolymer, ethylene/acrylic acid/VA copolymer, acrylates/VP copolymer, acrylates/VA copolymer, steareth-10 allyl ether/acrylatescopolymer, acrylates/steareth-50 acrylate copolymer, acrylates/steareth-20 methacrylate copolymer, acrylates/ammonium methacrylate copolymer, styrene/acrylates copolymer, styrene/acrylates/ammonium methacrylate copolymer, 10 ammonium styrene/acrylates copolymer, sodium styrene/acrylates copolymer, acrylates/hydroxyesters acrylates copolymer, betaine acrylate copolymers including methacryloyl ethyl betaine/acrylates copolymer, lauryl acrylate/VA copolymer, VA/butyl maleate/isobornyl acrylate copolymer, ethylene/methacrylate copolymer, vinylcaprolactam/VP/dimethylaminoethyl methacrylate copolymer, sodium acrylates/acrolein copolymer, VP/dimethylaminoethylmethacrylate copolymer, AMP-acrylates copolymer), where "VA" is "vinyl acetate" and "VP" is "vinyl polymer".

Polymers of acrylic acid and its salts (polyacrylic acid, ammonium polyacrylate, potassium aluminum polyacrylate, potassium polyacrylate, sodium polyacrylate) have similar properties and can be used in the practice of the present invention.

Other copolymers copolymerized with polyacrylates include polyacrylamide and PVA, sodium polyacrylate starch, acrylamide/sodium polyacrylate, hydroxyethyl acrylate/sodium acrylodimethyl taurate copolymer, acrylate copolymer, acrylamide/ammonium acrylate copolymer, acrylates/beheneth-25 methacrylate/steareth-30 methacrylate copolymer, polyvinyl alcohols (and derivatives or blends), PVP (derivatives and blends), sodium/carbomer, carbomer, TEA-carbomer, and acrylates/$C_{10-30}$ alkyl acrylate crosspolymer, to mention just a few.

Examples of commercially available polymers having an aliphatic backbone and a plurality of pendant groups thereon that are pendant ionic or ionizable groups, and/or that are pendant groups having at least one permanent dipole include Carbopols® Ultrez-10, Ultrez-20, Ultrez-21; Pemulen TR-1 and Pemulin TR-2 (all the foregoing available from Lubrizol Advanced Materials, Cleveland Ohio, USA); as well as Sepinov EMT-10 (distributed in the United States by SEPPIC Inc., Fairfield N.J.), to mention just a few.

Ionizable pendant groups are or include a functional group that includes, a labile ("acidic") hydrogen atom. The carboxyl group (—$CO_2H$), the sulfate group (—O—$SO_3H$), and the sulfite group (—$SO_3H$) are examples of functional groups that have labile hydrogen atoms and that can be, or be a constituent of, an ionizable pendant group. Polymers of acrylic acid, commonly referred to as "carbomers", are preferred polymers having an aliphatic backbone and a plurality of ionizable pendant groups that are useful in the cold process formulation aid of the present invention, in certain of its embodiments. Carboxyl functionality is found in fatty acids, which can be waxes.

Pendant groups having a permanent dipole include pendant groups that are or that include one or more of an alcoholic hydroxyl group, carboxylic group, thiolic thiol group, ester group, amide group, imide group, imine group, or nitrile group, to mention just a few. Examples of polymers having an aliphatic backbone and a plurality of pendant groups having a permanent dipole include poly(vinyl pyrrolidone), poly(vinyl alcohol), poly(methyl methacrylate), and copolymers of methyl acrylate and/or methyl methacrylate with alkyl esters of acrylic acid and/or methacrylic acid having about 10 to about 30 carbon atoms in the alkyl group, to mention just a few.

The plurality of pendant groups of the polymers having an aliphatic backbone and a plurality of pendant groups that are useful in the practice of the present invention, in certain of its embodiments, can include more than one type of pendant group selected, independently, from ionic, ionizable, and permanent-dipole-including pendant groups. To mention just one example, such polymer can have both alkyl ester and carboxyl pendant groups. Such polymer can also have more than one species of the same type or genus of pendant group. For example, such polymer can have both carboxyl and sulfate ionizable pendant groups, to mention just one example. Amines—either non-neutralized or partially or totally neutralized with an inorganic or organic base, or quaternized—are also ionizable. As will be understood by the person having ordinary skill in the art, when ionizable groups, when subjected to the action of a base, give anionic groups (e.g., carboxyl groups) and when subjected to the action of an acid or quaternization, give cationic groups (e.g., tertiary amine). Neutralization of the anionizable groups (or cationizable groups respectively) with the base (or the acid respectively) may be carried out partially or completely, depending on the amounts of neutralizing agents used.

The term "quaternary ammonium" is common chemical nomenclature and its meaning will be understood by one skilled in the art. There are two types of ammonium compounds: acidic, and non-acidic. Acidic ammonium compounds are acid salts of amines, and are characterized by having an N—H covalent bond wherein the N—H bond is reactive with and may protonate bases. Non-acidic, or "quaternary" ammonium compounds do not have this N—H bond, and are not reactive with bases in the same way. Quaternary ammonium compounds are generally characterized by having four covalent bonds, usually four carbon-nitrogen bonds attached to the positively-charged central nitrogen. Quaternary ammonium polymers are also known as "polyquats" or "polyquaterniums". Non-limiting examples of "polyquats" suitable for use in the cold process formulations aids of the present invention and methods of using the same include: Polyquat 6—Poly(diallyl-dimethyl-ammonium chloride); Polyquat 7, a copolymer of acrylamide and diallyldimethyl-ammonium chloride; Polyquat 11, a copolymer of vinylpyrrolidone and quarternized dimethyl-aminoethyl methacrylate; Polyquat 32—Poly(acrylamide 2-methacryloxyethyltrimethyl ammonium chloride); Polyquat 37—Poly(2-methacryloxyethyltrimethylammonium chloride); Polyquat 67—Polymer of hydroxyethyl cellulose with dimethyldodecylammonium and trimethylammonium.

In certain embodiments of this aspect of the present invention—in which the polymer component of the CPFA is an aliphatic backbone having a plurality of pendant groups thereon that are pendant ionic or ionizable groups—the CPFA is "eutectic", a term that the person of ordinary skill in the art will understand to mean a mixture of chemical compounds forming a single chemical composition that solidifies at a lower temperature than any material in the composition. In characterizing certain CPFA compositions of the present application as "eutectic", the inventors mean that these CPFAs solidify at a lower temperature than any material in the composition (i.e., its component parts). The eutectic nature of certain CPFAs of the present invention is demonstrated by differential scanning calorimetry, which shows the CPFA has a single melt/freeze point.

In eutectic embodiments of the present invention, CPFAs are produced by the process of combining at least two components— (i) at least one wax component and (ii) at least one polymer component having an aliphatic backbone and a plurality of pendant groups thereon that are pendant ionic or ionizable groups, or pendant groups having at least one permanent dipole that includes an acid, alcohol, thiol, ester, amine, amide, imide, imine, or nitrile moiety—at a temperature that is at least about 5° C. above (a) the higher of the melting point of the wax (or in CPFAs containing more than one wax, the wax with the highest melting point) or (b) the softening point of the polymer component having an aliphatic backbone with a plurality of pendant ionic or ionizable groups (or in CPFAs containing more than one polymer component having an aliphatic backbone and a plurality of pendant ionic or ionizable group groups thereon, the polymer having the highest softening point). For purposes of describing eutectic embodiments of the present invention, and the process for making the same, the term "softening point" is to be understood to mean a temperature at which a material softens to a specified extent. Softening point can be determined, for example, by the Vicat method (ASTM-D 1525 or ISO 306), Heat Deflection Test (ASTM-D648) or a ring and ball method (ISO 4625 or ASTM E28-67/E28-99 or ASTM D36 or ASTM D6493-11).

In certain eutectic embodiments of the present invention, in which the highest melting point of the wax component(s) is a temperature that is higher than the highest softening point of the polymer component(s), the CPFA is formed by a process in which the wax component(s) and the polymer component(s) are combined at a temperature that is at least about 5° C. higher than the highest melting point of the wax component(s).

In other eutectic embodiments of the present invention, in which the highest softening point of the polymer component(s) of the CPFA is a temperature that is higher than the highest melting point of the wax(es), the CPFA is formed by a process in which the wax component(s) and the polymer component(s) are combined at a temperature that is at least about 5° C. higher than the highest softening point of the polymer component(s).

Eutectic CPFA of the present application can, and preferably are made by a process involving the following sequential steps:

(i) add wax(es) to a vessel; heat to a temperature of at least about 5° C. above the melt point of the highest melt point wax; mix until a homogenous batch of molten wax(es) is achieved;

(ii) add polymer(s) having an aliphatic backbone with a plurality of pendant ionic or ionizable groups to the batch of molten wax(es) from step (i) while heating to a temperature of at least about 5° C. above the highest melt point of the wax(es) or the highest softening point of the polymer(s); mix until a homogenous eutectic mixture is formed;

(iii) cool the eutectic mixture from step (ii) to a temperature of about 5° C. above the congealing point of the mixture;

(iv) pour the eutectic mixture from step (iii) onto a chilled surface having a temperature from about −10° C. to about 10° C., producing a CPFA in the form of a solid wax, or wax-like substance.

The solid wax (or wax-like substance) produced by the above-described process can be poured and cast into a block, flaked, or prilled, and, optionally, ground to smaller particle size and/or passed through a sieve to achieve a desired particle size cut-off.

In preferred embodiments of the present invention, in step (iii) the polymer(s) having an aliphatic backbone with a plurality of pendant ionic or ionizable groups start to soften at a temperature of about 30° C., with near complete softening achieved at a temperature typically ranging from about 60° C. to about 120° C.

In certain embodiments of the first aspect of the invention directed to eutectic CPFAs, where the polymer having an aliphatic backbone is an acrylic acid that has been pre-neutralized, a salt of a polyacrylic ester (e.g., sodium polyacrylate), or a salt of an acrylic acid, and the wax is not micronized and is not emulsifying, the ratio, by weight, of the non-micronized/non-emulsifying wax to the polymer having an aliphatic backbone is from about 60:40 to 80:20, and if the wax is a micronized wax or a emulsifying wax, the ratio, by weight, of wax to polymer backbone is 70:30 to 98:2.

In other embodiments of the first aspect of the invention directed to eutectic CPFAs, where polymer having an aliphatic backbone is an acrylic acid or polyacrylic acid, and the wax is not micronized and is not self-emulsifying, the ratio, by weight, of the non-micronized/non-emulsifying wax to the polymer having an aliphatic backbone is, in preferred embodiments, from about 70:30 to 95:5, and if the wax is a micronized wax or a emulsifying wax, the ratio, by weight, of wax to polymer backbone is, in preferred embodiments, from about 90:10 to 99.5:0.5. All ratios refer to Wax:Polymer compositions. It will be understood by the skilled artisan that the above preferred embodiments relate to CPFAs which are comprised of a high wax content (at least about 70), where the CPFA does not contain an emulsifying wax, and where the CPFA is to be added to an aqueous medium at room temperature. As described elsewhere in the present application, the amount of wax can be increased (and correspondingly the amount of polymer can be decreased) if an emulsion or hydrogel is to be formed at or near the eutectic point of the CPFA. By way of non-limiting example, if a CPFA can have a wax:polymer ratio of 70:30, a CPFA can also be made within the scope of the present invention with the same wax and polymer but at different ratios, for example 80:20, if the emulsion is to be formed at or near the eutectic point. It will also be understood that a CPFA having a higher polymer content—for example 60:40—could be used to form an emulsion at ambient temperature.

A second aspect of the present invention is directed to cold process formulation aids and methods employing the same for rendering polyacrylic acids, polyacrylates, polycacrylate copolymers, polyacrylate crosspolymers, and their respective salts (collectively referred to in the present application as "Polyacrylic Acid Derivatives" and abbreviated as "PADs") directly soluble in cosmetically-acceptable esters and Caprylic/Capric Glycerides (CTG), without using a petroleum-derived solvent.

Caprylic/Capric Triglyceride (abbreviated "CTG") is a medium chain triglyceride esterified from caprylic and capric acids and glycerine. CTG is an article of commerce available from suppliers of chemical raw materials used in the formulation of personal care and pharmaceutical products, including from Jeen International Corp. (Fairlawn, N.J.) under the tradename JEECHEM® CTG.

The inventive compositions according to this aspect of the present invention are cold process formulation aids comprising (a) at least one PAD and (b) at least one emulsifying wax.

A non-limiting list of emulsifying waxes suitable for use in this aspect of the invention are provided above.

In certain preferred embodiments of this aspect of the invention, the emulsifying wax is a polyglyceryl ester. Polyglyceryl esters are liquid, non-ionic surfactants based on linear polyglycerol and fatty acids.

Particularly preferred polyglyceryl esters include Polyglyceryl Monostearate, Polyglyceryl-3 Stearate, Polyglyceryl-6 Distearate Hexaglyceryl Distearate, Decaglyceryl Dipalmitate, all commercially available from, Lonza, Inc. (Allendale, N.J.; among other suppliers of raw materials used in the manufacture of personal care products) under the tradename Polyaldo.

Polyglycerol-3 (also known as Polyglycerin-3) is a clear yellowish viscous liquid with an average molecular weight of 250 g/mol. Polyglycerin-3 is a glycerin polymer containing 3 glycerin units. It is water-soluble and is less hygroscopic than glycerol or diglycerol.

Polyglycerin-6 is a glycerin polymer containing 6 glycerin units.

Polyglyceryl-3 Stearate is an ester of stearic acid and Polyglycerin-3 and has the empirical formula $C_{27}H_{54}O_8$. Polyglyceryl-3 Stearate is an article of commerce available from suppliers of chemical raw materials to formulators of personal care and pharmaceutical products, including under the tradenames Caprol™ 3GS from Abitec Corporation (Columbus, Ohio), Akoline™ PG 7 from AarhusKarlshamn AB, and as Polyaldo™ TGMS KFG (3-1-S) from Lonza (Allendale, N.J.).

Polyglyceryl-6 Distearate is a diester of stearic acid and Polyglycerin-6 and is available under the tradenames Caprol 6G2S from Abitec Corporation (Columbus, Ohio), Plurol Stearique WL 1009 from Gattefosse s.a.s. (Saint Priest, France) and Polyaldo HGDS KFG (6-2-S) from Lonza Inc. (Allendale, N.J.).

As used herein, by the term "directly soluble" in cosmetically-acceptable oil or CTG is meant that the inventive composition comprising a PAD/emulsifying wax blend can be added to a cosmetically-acceptable oil or CTG and does not form aggregates, the PAD is not visually perceptible with the naked eye as a powder or crystal, and the resulting mixture of PAD/emulsifying wax and cosmetically-acceptable oil or CTG does not leave a gritty hard feel when applied to the skin. Non-limiting examples of cosmetically-acceptable esters into which the inventive blend of PAD/emulsifying wax are directly soluble are set out below.

Cosmetically-acceptable monoesters into which the CPFA of the second aspect of the present invention—blend of PAD(s)/emulsifying wax(es)—are directly soluble include, but are not limited to, hexyldecyl benzoate, hexyl laurate, hexadecyl isostearate, hexydecyl laurate, hexyldecyl octanoate, hexyldecyl oleate, hexyldecyl palmitate, hexyldecyl stearate, hexyldodecyl salicylate, hexyl isostearate, butyl acetate, butyl isostearate, butyl oleate, butyl octyl oleate, cetyl palmitate, ceyl octanoate, cetyl laurate, cetyl lactate, isostearyl isononanoate, cetyl isononanoate, cetyl stearate, stearyl lactate, stearyl octanoate, stearyl heptanoate, and stearyl stearate. As will be understood by the skilled artisan, in the above nomenclature, the first term indicates the alcohol and the second term indicates the acid in the reaction. For example, stearyl octanoate is the reaction product of stearyl alcohol and octanoic acid.

Non-limiting examples of cosmetically-acceptable diesters into which the CPFA blend of PAD(s)/emulsifying wax(es) of the present invention are directly soluble include, but are not limited to, diisostearyl malate, neopentyl glycol dioctanoate, dibutyl sebacate, di-$C_{12-13}$ alkyl malate, dicetearyl dimer dilinoleate, dicetyl adipate, diusocetyl adipate, diisononyl adipate, diisostearyl dimer dilinoleate, disostearyl fumarate, diisostearyl malate.

Cosmetically-acceptable triesters into which the CPFA blend of PAD(s)/emulsifying wax(es) of the present invention are directly soluble include, but are not limited to, triarachidin, tributyl citrate, triisostearyl citrate, tri-$C_{12-13}$ alkyl citrate, tricaprylin.

In accordance with the first aspect of the present invention, the cold process formulation aid, in other of its embodiments, includes a polymer having a polysaccharide backbone and a plurality of pendant ionizable or ionic groups selected from carboxyl groups, sulfate groups, salts of either, or combinations thereof. The polysaccharide backbone can include either or both of pyranoside and furanoside residues. Important is that the polysaccharide backbone have a plurality of pendant ionizable or ionic groups selected from carboxyl groups, sulfate groups, salts of either, or combinations thereof. Preferred are polysaccharides that swell in water at room temperature, non-limiting examples of which include sodium alginate, carrageenan, carboxymethyl cellulose, xanthan, starches, and cationic guar. Anionic and cationic polysaccharides suitable for use in the present invention include, but are not limited to the following: anionic polysaccharides—alginic acid, pectin, xanthan gum, hyaluronic acid, chondroitin sulfate, gum arabic, gum karaya, gum tragacanth, carboxymethyl-chitin, cellulose gum; cationic polysaccharides—chitosan, cationic guar gum, cationic hydroxyethylcellulose. Amphoteric polysaccharide compounds containing both cationic and anionic polymer chain(s) may also be used in accordance with the compositions and methods of the present invention. Non-limiting examples of such polymers include carboxymethylchitosan, N-hydroxy-dicarboxyethyl-chitosan, cetyl hydroxyethylcellulose. Amphoteric polysaccharide compounds may also be obtained by grafting and polymerization monomers corresponding onto anionic polysaccharides, and include polymers of the type disclosed in PreGrant US Patent Application Publication 2008/0260674. Non-limiting examples of cationic polysaccharides suitable for use in the cold process formulations aids of the present invention and methods of using the same include: guar hydrpropyl trimonium chloride; 2-hydroxy-3-(trimethylammonio) propyl ether chloride; locust bean hydroxypropyl trimonium chloride; and Casalpina spinosa hydroxypropyl trimonium chloride.

The cold process formulation aid of the present invention, in other of its embodiments, includes salts of esters, have one or a plurality of ionizable groups. Poly(aspartate) for example, perform the same function as, and are claimed to be an even more eco-friendly alternative to, the polymers having an aliphatic backbone and a plurality of pendant groups thereon that are pendant ionic or ionizable groups and discussed above. Sodium poly(aspartate), frequently referred to in the trade as simply poly(aspartate), is particularly useful in the practice of the present invention.

In still further embodiments, the cold process formulation aid of the present invention includes a combination of one or more polymers having an aliphatic backbone and a plurality of pendant groups thereon that are pendant ionic or ionizable groups, one or more a polymer having a polysaccharide backbone and a plurality of pendant ionizable or ionic groups selected from carboxyl groups, carboxylate groups, sulfate groups, and salts thereof, and/or poly(aspartate). One non-limiting example of such a CPFA contains cetyl alcohol, glyceryl monostearate, sodium polyacrylate, and xanthan gum. In yet further embodiments, the cold process formulation aid of the present invention includes one or more polymers having a silicone backbone with pendant ionic or ionizable groups, and/or that are pendant groups having at least one permanent dipole that includes an alcohol, thiol, ester, amide, amine, imide, imine, or nitrile moiety. Examples of such polymers include amodimethicone and dimethiconol, to mention just two.

Polymers having pendant ionic or ionizable groups can be referred to as polyelectrolytes.

The cold process formulation aid of the present invention according to the first aspect of the invention, in all of its embodiments, includes at least one wax. Waxes are substances which are solid or semi-solid at room temperature, that undergo a reversible solid-liquid change of state, with a melting point of greater than or equal to about 30° C., and up to about 150° C., and in some embodiments up to about 170° C., and in still other embodiments up to about 200° C., and have an anisotropic crystal organization in solid form. Preferably, the wax has a melting point of 35° C. to 100° C. But waxes having a melting point >100° C. or waxes having a melting point at or below room temperature (e.g., cocoa butter) can be used in particular embodiments of the present invention.

The skilled artisan knows that waxes of commerce rarely have a sharp melting point such as exhibited by, for example, purified organic compounds, and that the melting point of a wax may vary depending on the test method used. The well-known technique of differential scanning calorimetry (DSC) can be used to determine the melting point of a wax. DSC can, for example, be performed using a 5 mg sample and a heating rate of 10° per minute. In this example, the temperature at which the melting endotherm shows a maximum deviation from baseline (i.e. the "peak temperature") is taken as the melting point.

Waxes useful in the practice of the present invention can be classified by source or chemical structure. Waxes useful in the practice of the present invention can be either hydrogenated (fully or partially) or non-hydrogenated natural waxes, such as those obtained from animal, botanical, or mineral sources, or they can be synthetic waxes. Some synthetic waxes are synthesized using one or more components from natural sources. Synthetic waxes can include more than one wax, each from a different source or of a different chemical class or structure, or they can be a natural wax that has been compounded with other components to obtain a synthetic wax.

Natural waxes that are animal waxes include beeswax, lanolin, shellac wax, and whale wax. Natural waxes that are botanical waxes include candelilla wax, castor wax, cotton wax, soy wax, jojoba wax, olive wax, carnauba wax, sugar cane wax, rice bran wax, bayberry wax, sunflower wax, rose petal wax, and Japan wax. Sunflower wax is a preferred botanical wax for use in the practice of certain embodiments of the cold process formulation aid of the present invention.

Mineral waxes include montan wax, ozokerite, and ceresin.

Petroleum-based waxes include paraffin wax and microcrystalline wax.

Synthetic waxes include polyethylene waxes (e.g. Jeenate® waxes available from Jeen International of Fairfield N.J., USA), silicone waxes, fluoro waxes, Fischer-Tropsch waxes, polypropylene waxes, esters of poly(ethylene glycol), and pegylated sorbitans, alone or in combination with, for example, monoalkyl ethers of poly(ethylene glycol) (e.g. ceteareth-20). Synthetic waxes also include so-called "functionalized waxes, a non-limiting example of which are pegylated animal waxes (e.g. PEG-8 beeswax)

In certain embodiments of the cold process formulation aid of the present invention, the wax is a synthetic emulsifying wax, for example glyceryl monostearate, to mention just one. Self-emulsifying wax, as that term is used herein, refers to a chemically modified wax that contains at least one emulsifier component, e.g., a non-ionic emulsifier.

The wax component of the self-emulsifying wax contains one or more cosmetically or dermatological acceptable waxes from among waxes of animal origin, waxes of plant origin, waxes of mineral origin and waxes of synthetic origin. Examples of waxes of animal origin include beeswaxes, lanolin waxes and Chinese insect waxes. Examples of waxes of plant origin include rice waxes, olive wax, carnauba wax, candellila wax, sugar cane waxes, Japan waxes, and cotton wax. Examples of waxes of mineral origin include paraffins, microcrystalline waxes, montan waxes and ozokerites. Examples of waxes of synthetic origin include polyolefin waxes, e.g., polyethylene waxes, waxes obtained by Fischer-Tropsch synthesis, waxy copolymers and their esters, and silicone and fluoro waxes.

Alternatively, hydrogenated oils of animal or plant origin (natural waxes) may be present in the self-emulsifying wax in combination with synthetic compounds. Thus, synthetic waxes useful in the practice of the present invention include substances that can include components from natural sources.

Waxes also include esters of long-chain primary alcohols and fatty acids, as well as shea butter and cocoa butter. Accordingly, certain fats or butters are to be understood as waxes within the scope of the present invention, since these materials require an increase in temperature to cause a phase transition from a semi-solid or solid to a liquid. Typically, the melt point for fats and butters considered as waxes within the scope of the present invention is less than about 50° C. At that temperature, a fat or butter can be converted to a wax if the fat or butter is hydrogenated, partially or fully. A non-limiting example of a fat to be considered a wax for purposes of the present invention is castor oil.

Self-emulsifying waxes may be obtained commercially from numerous manufacturers and suppliers. Commercially available self-emulsifying waxes that may be useful in the practice of the present invention include ethoxylated and/or propoxylated waxes as well as the following: PEG-20 sorbitan beeswax (Atlas G-1726, Uniqema; Nikkol GBW-125, Nikko), PEG-6 beeswax (ESTOL 375, Uniqema), PEG-8 beeswax (Apifil, Gattefosse), Olivem 1000 (Cetearyl Olivate, Sorbitan Olivate, from B&T SRL), PEG-12 beeswax and PEG-12 carnauba wax.

In certain embodiments, the wax—regardless of source or type—is micronized. That is, the wax is used in the form of particles having an average particles size, as determined by particle size analyzers known in the art, including those available from Malvern, of about 50µ or less. When micronized waxes are used, additional options for making the cold process formulation aid of the present invention, discussed below, can be used. Micronized waxes useful in the practice of the present invention include Ceridust® micronized poly (ethylene) (Clariant), Micropoly® micronized poly(ethylene) wax (Micro Powders, Inc.), Microease® micronized synthetic waxes (MicroPowders, Inc.), and Microcare® waxes (MicroPowders, Inc) that include natural waxes (e.g. carnauba wax), to mention just a few. Anticaking agents, such as silicas or a harder wax, can be added to a softer wax. Additionally, plasticizers (e.g., esters or oils) may be added to the wax before micronization. As used in the present invention a "plasticizer" means a compound present in an amount sufficient to lower the glass transition temperature of the CPFA. Glass transition is measured using a differential scanning calorimeter. To evaluate the reduction in the glass transition temperature caused by the plasticizer, the glass transition temperature of the CPFA is first measured by a method known to the person skilled in the art, and a mixture of the CPFA and the plasticizer is then prepared and a measurement is taken by the same method under the same conditions.

The plasticizing compound may be chosen especially from aliphatic or aromatic polycarboxylic acid esters of aliphatic or aromatic alcohols comprising from 1 to 10 carbon atoms, as well as silicone oils. Non-limiting examples of plasiticizers include liquid paraffin, isoparaffin, hexyl laurate, isopropyl myristate, myristyl myristate, cetyl myristate, 2-octyldodecyl myristate; isopropyl palmitate, 2-ethylhexyl palmitate, butyl stearate, decyl oleate, 2-octyldodecyl oleate, myristyl lactate, cetyl lactate, lanolin acetate, stearyl alcohol, cetostearyl alcohol, oleyl alcohol, avocado oil, almond oil, olive oil, cocoa oil, jojoba oil, gum oil, sunflower oil, soybean oil, camellia oil, squalane, castor oil, mink oil, cottonseed oil, coconut oil, egg yolk oil, beef tallow, lard, polypropylene glycol monooleate, neopentyl glycol 2-ethylhexanoate or a similar glycol ester oil; triglyceryl isostearate, the triglyceride of a fatty acid of coconut oil, or a similar oil of a polyhydric alcohol ester; polyoxyethylene lauryl ether, polyoxypropylene cetyl ether or a similar polyoxyalkylene ether.

In certain embodiments, the plasticizer may be a silicone oil, non-limiting examples of which include a dimethylpolysiloxane with the two molecular ends capped with trimethylsiloxy groups, a copolymer of methylphenylsiloxane and of dimethylsiloxane having the two molecular ends capped with trimethylsiloxy groups, a copolymer of methyl-3,3,3-trifluoropropylsiloxane and of dimethylsiloxane having the two molecular ends capped with trimethylsiloxy groups, or similar unreactive linear silicone oils, and also hexamethyl-cyclotrisiloxane, octamethylcyclo-tetrasiloxane, decamethylcyclopentasiloxane, dodecamethylcyclohexasiloxane or a similar cyclic compound. In addition to the unreactive silicone oils, modified polysiloxanes containing functional groups such as silanol groups, amino groups and polyether groups on the ends or within the side molecular chains may be used.

Powders such as mica, calcium carbonate, silica, can be used as plasticizers.

Differential scanning calorimetry demonstrates that the heat of disassociation of the wax component of the cold process formulation aid is different than the heat of disassociation of the cold process formulation aid itself, the latter being lower. This difference is important both in terms of sensorial properties and rheological profiles of the final commercial product (i.e., the emulsion or hydrogel). By way of non-limiting example, the viscosity of an emulsion containing a wax (W) and polymeric thickener (P) formed by conventional processes (i.e., heating) is lower than the viscosity of an emulsion formed without heat (i.e., at room temperature) by adding a cold process formulating aid (WP) consisting essentially of the same wax and same polymeric thickener at the same concentrations as used in the conventional (i.e., heated) emulsion.

The cold process formulation aid of the present invention can be obtained in powder form, a preferred physical form, by combining one or more polymers having an aliphatic backbone and a plurality of pendant groups thereon that are pendant ionic or ionizable groups, one or more polymers having a polysaccharide backbone and a plurality of pendant ionizable or ionic groups selected from carboxyl groups, carboxylate groups, sulfate groups, and salts thereof, or poly(aspartate), or a combination of the foregoing, with at least one wax in a spray drying (also known as spray congealing when heat, rather than a solvent, is being removed), jet milling or prilling process. If the wax is a micronized wax micronized to an average particle size of about 5μ, a dry blending process can suffice.

In the spray drying process, the one or more polymers having an aliphatic backbone and a plurality of pendant groups thereon that are pendant ionic or ionizable groups, the one or more polymers having a polysaccharide backbone and a plurality of pendant ionizable or ionic groups selected from carboxyl groups, carboxylate groups, sulfate groups, and salts thereof, the poly(aspartate), or a combination of the foregoing are combined with one or more molten waxes at about 30° C. to about 150° C., and in in some embodiments up to about 170° C., and in still other embodiments up to about 200° C. and the combination converted to a powder by spray congealing.

The technique of spray-drying is well known in chemical engineering and is summarized, for example, in R. P. Patel et al., 2 *Indian Journal of Science and Technology*, Vol. No. 2, 44-48 (2009). The skilled artisan knows to adjust the temperature of the molten wax, the nozzle orifice size, and the atomizing pressure to obtain the desired particle size in the final powder product. Preferred particle sizes are in the range of 5μ to 5 mm, more preferably 5μ to 50μ.

Prilling is likewise a technique for forming particulate or granular solid particles and is well known in chemical engineering. Prilling is accomplished in a prilling tower in which droplets of a molten combination of one or more waxes with polymers having an aliphatic backbone and a plurality of pendant groups thereon that are pendant ionic or ionizable groups, one or more polymers having a polysaccharide backbone and a plurality of pendant ionizable or ionic groups selected from carboxyl groups, carboxylate groups, sulfate groups, and salts thereof, poly(aspartate), or a combination of the foregoing, are allowed to fall under the action of gravity through the tower against a static or dynamic column of gas, for example air or nitrogen. The height of the prilling tower, the temperature of the gas, and the size of the droplets are adjusted, by routine experimentation, according to the melting point of the wax and the desired size of the final prill.

The cold process formulating aids of the present invention may vary in physical forms ranging from coarse powder to flake and pastille, which, in turn, can be further reduced in size using a jet mill.

When the wax is not a micronized wax and the cold process formulation aid of the present invention is made by spray drying or prilling, the ratio, by weight, of the one or more waxes to the one or more polymers (i.e. the one or more polymers having an aliphatic backbone and a plurality of pendant groups thereon that are pendant ionic or ionizable groups, the one or more polymers having a polysaccharide backbone and a plurality of pendant ionizable or ionic groups selected from carboxyl groups, carboxylate groups, sulfate groups, and salts thereof, the poly(aspartate), or a combination of the foregoing) is preferably from about 60:40 to 80:20.

When a micronized wax having an average particle size not exceeding about 50µ, is used, the cold process formulation of the present invention can be made by a dry blending process. In this case, the ratio, by weight, of one or more waxes to the one or more polymers is from about 85:15 to about 98:2. The dry blending can be accomplished using a ribbon mixer, a twin-shell mixer or a high intensity mixer. Micronized waxes can be used when the polymer is be sensitive to higher temperatures since these can be destroyed by high temps.)

The cold process formulation aid made by any of the above-described methods is preferably in the form of an easily-handled powder. However, the cold process formulation aid of the present invention, in certain embodiments, can also be provided in the form of a paste or a semi-solid having a butter-like consistency. When a paste form is desired, waxes or fats having a melting point near or below room temperature, e.g. shea butter or especially cocoa butter, are included in the formulation, especially in combination with other waxes (e.g. beeswax). The cold process formulation aid of the present invention in paste form can be made using conventional compounding equipment, for example a Banbury mixer.

In still further embodiments, the present invention provides a cold process for making personal care products that includes the step of combining the cold process formulation aid of the present invention with an aqueous medium and other ingredients.

Additional ingredients that may be added to emulsions formed with the cold process formulation aids of the present invention include, but are not limited to, oils and esters (as plasticizers); iron oxides; capric caprylic triglyceride; glycerine; emulsifiers (polysorbate); silicone compounds, including volatile silicones, elastomers and resins silicone cross-polymer (Dow Corning 9506). A paste can also be made that contains a level of aqueous medium at levels lower than those of the intended finished formula. All of the aforementioned embodiments can be manufactured to a thick paste or cream that can contain 0.1 to 70% of an aqueous medium or water. This can be considered to be a "concentrate" that can be let down or diluted to a higher level of aqueous medium or water. Said concentrate can be used to make emulsions.

In another embodiment, the present invention provides a method of making a personal care product, without heating, that includes the steps of (i) combining with an aqueous medium, in certain, but not all embodiments, at a temperature not exceeding 30° C., a polymer having an aliphatic backbone and a plurality of pendant groups thereon that are pendant ionic or ionizable groups, or pendant groups having at least one permanent dipole that includes an acid, alcohol, thiol, ester, amines, amide, imide, imine, or nitrile moiety, thereby forming a hydrogel and (ii) adding a micronized wax, having a mean particle size from 5 to 50 microns, to the hydrogel of step (i).

Polymers having a polysaccharide backbone and a plurality of pendant ionizable or ionic groups selected from carboxyl groups, carboxylate groups, sulfate groups, and salts thereof, or polyaspartate can be substituted for the polymer having an aliphatic backbone in the above process. Non-limiting examples of polysaccharides having a pendant ionizable or ionic groups include dehydroxanthan sold as Amaze XT from AkzoNobel.

As is known in the dermatologic arts, surfactants can be irritating or negatively impact active ingredients (e.g., by denaturing proteins). In a still further embodiment, the cold process formulation aid of the present invention provides a method of making a personal care product that is essentially free of ethoxylated surfactants, and in certain embodiments essentially of free of surfactants. By "essentially surfactant-free" is meant that no surfactant is added to the emulsion, other than surfactant(s), if any, present in the CPFA itself.

The present invention, in certain of its embodiments, is illustrated by the following non-limiting examples.

Example 1—First Process for Making a Cold Process Formulation Aid with Non-Micronized Wax and a Polyelectrolyte Polymer Non-micronized wax and an oil are melted together. A polyelectrolyte polymer having an aliphatic backbone and a plurality of pendant groups thereon that are pendant ionic or ionizable groups, or pendant groups having at least one permanent dipole that includes an alcohol, thiol, ester, amide, imide, imine, or nitrile moiety is combined with the molten wax. The polyelectrolyte polymer constitutes about 30% by weight of the combination. The combination is then cooled to a continuous solid mass and comminuted to the desired particle size.

In a modification of the first process, the molten combination of wax and polyelectrolyte polymer is not cooled to a continuous solid mass. Instead, the molten combination is passed through a spray drying apparatus to cool and spray congeal the combination to a powder.

In another modification of the first process, the molten combination is passed through a prilling tower to cool the combination and obtain a prin.

Example 2—Second Process for Making a Cold Process Formulation Aid with a Micronized Wax and a Polyelectrolyte Polymer Wax is micronized by jet mill pulverization to an average particle size of about 5µ. The micronized wax is dry blended with a polyelectrolyte polymer having an aliphatic backbone and a plurality of pendant groups thereon that are pendant ionic or ionizable groups, or pendant groups having at least one permanent dipole that includes an alcohol, thiol, ester, amide, imide, imine, or nitrile moiety to obtain the cold processing aid. The polymer having an aliphatic backbone and a plurality of pendant groups thereon that are pendant ionic or ionizable groups, or pendant groups having at least one permanent dipole that includes an acid, alcohol, thiol, ester, amine, amide, imide, imine, or nitrile moiety constitutes about 5% by weight of the dry-blended combination.

Example 3—Third Process for Making a Cold Process Formulation Aid Using a Non-Micronized Wax, a Polyelectrolyte Polymer, and a Silicone Crosspolymer Wax and a polyelectrolyte polymer (described in the previous examples) are melted together. Dow DC 9506 (a silicone cross polymer) is combined with the molten wax and the polyelectrolyte polymer. The molten combination is cooled to obtain a continuous solid mass that is comminuted to the desired particle size.

In a modification of the third process, the molten combination of wax, polyelectrolyte, polymer and silicone crosspolymer is not cooled to a continuous solid mass. Instead, the molten combination is passed through a spray drying apparatus to cool and spray congeal the combination to a powder.

In another modification of the third process, the molten combination is passed through a prilling tower to cool the combination and obtain a prin.

Example 4—Fourth Process for Making a Cold Process Formulation Aid

In a fourth process, a molten combination of polyelectrolyte and wax is further combined with oil phase ingredients (esters, natural oils, synthetic oils, butters (e.g., partially hydrogenated vegetable oils), silicone compounds) and/or hydrophilic ingredients (e.g., glycols) to make a paste or slurry, optionally with a surfactant. Two non-limiting examples of this process are as follows: (1) combine Beewax with Sodium Acrylate/Sodium Acryloyldimethyl Taurate Copolymer, Isohexadecane and Polysorbate 80; (2) combine Sunflower wax with Hydroxyethylacrylate/Sodium Acryloyldimethyl Taurate Copolymer.

Any of the above-mentioned processes may comprise the further step of pre-hydrating the cold process formulation aid of the present invention (i.e., by adding water). CPFAs of this type are available under the tradename CPW-JAW, "just add water", from Jeen International Corp. (Fairfield, N.J.). CPFAs of this type would form a concentrate and, in preferred embodiments, would include one or more preservatives known to the skilled artisan. In addition to water, a final product (e.g., lotion, cream) can be made by adding other ingredients, including, for example, anti-aging skin care active ingredient as described below.

Cold Process Formulation Aids (Examples 5-21)

Example 5—Polyethylene (70%); Sodium Polyacrylate (30%)
Example 6—Sunflower Wax (70%); Sodium Polyacrylate (30%)
Example 7—Yellow Beeswax (70%); Sodium Polyacrylate (30%)
Example 8—Cocoa Butter PPP (35%); Yellow Beeswax (35%); Sodium Polyacrylate (30%)
Example 9—Polyethylene (45%); Polyvinylpyrrolidone (25%); Sodium Polyacrylate (30%)
Example 10—Stearic Acid (30%); Ceteareth-20 (7%); Cetearyl Alcohol (62%); Sodium Polyacrylate (1%)
Example 11—Stearic Acid, (32%); Cetearyl Alcohol (32%); Glyceryl Stearate (21%); Peg-100 Stearate (10%); Sodium Polyacrylate (5%)
Example 12—Cetearyl Alcohol (70%); Polysorbate 60 (25%); Sodium Polyacrylate (5%)
Example 13—Cetyl Alcohol (50%); Sodium Acrylate Acryloyl Dimethyl Taurate Copolymer (30%); Glyceryl Monostearate (15%); Caprylic/Capric Triglyceride (5%)
Example 14—Stearic Acid (99%); Sodium Acrylate Acryloyl Dimethyl Taurate Copolymer (1%)
Example 15—Sunflower wax (35%); Shea butter (35%); Sodium Polyacylate (30%)
Example 16—Polyethylene (35%); Sodium Polyacrylate (30%); Iron Oxides (15%); Titanium Dioxide (20%)
Example 17—Polyethylene (50%); Sodium Polyacrylate (30%); Dimethicone/Vinyl Dimethicone Crosspolymer (20%)
Example 18—Sunflower Wax (70%); Acrylates/$C_{10\text{-}30}$ Alkyl Acrylate Crosspolymer (30%)
Example 19—Sunflower wax (50%); Caprylic/Capric Triglyceride (20%); Guar Gum (30%)
Example 20—Sunflower wax (50%); Caprylic/Capric Triglyceride (20%); Carrageenan (30%)
Example 21—Sunflower wax (50%); Caprylic/Capric Triglyceride (20%); Sodium Alginate (30%).

The ratios of the component parts of the CPFAs (i.e., polymeric backbone, synthetic or natural, and wax) vary depending on the type of wax and the manufacturing process (e.g., jet milling). Dry blended CPFAs, irrespective of whether the wax is functionalized, can have ratios of as low as 0.5% polymer. Molten CPFAs containing emulsifying waxes (e.g., fatty acids, fatty alcohols) can also have as low as 0.5% polymer content. Molten CPFAs containing non-emulsifying waxes can, preferably have 20% or higher polymer content, although Molten CPFAs having a lower polymer content can be used in accordance with the cold process methods of the present invention.

Example 22—Swollen Silicone Oil Gel

The cold process formulation aid of Example 3 is dispersed in water in a suitable vessel at a temperature not above about 30° C. When the processing aid is dispersed, the desired amount of silicone oil is added at a temperature not exceeding about 30° C. to obtain a gel swollen with the silicone oil.

Examples of CPFAs in accordance with the second aspect of the invention, in which a blend of PAD(s)/emulsifying wax(es) is directly soluble in cosmetically-acceptable ester (s) or CTG include the following:

Example 23

A CPFA consisting essentially of 10% Polyglyceryl-3 Stearate, 30% Isostearyl Neopentanoate, and 60% Sodium Polyacrylate Example 24

A CPFA consisting essentially of 10% Polyglyceryl-3 Stearate, 30% Isostearyl Neopentanoate, and 60% Polyquarternium 37.

Example 25

A CPFA consisting essentially of 20% Sorbitan Stearate, 30% Isopropyl Isostearate, and 50% Polyquaternium 10.

Example 26

A CPFA consisting essentially of 15% Polyglyceryl-6 Distearate, 25% $C_{12\text{-}C15}$ Alkyl Benzoate, and 60% Sodium Alginate.

Example 27

CPFAs in accordance with the second aspect of the invention (Examples 23-26) are generally made by adding the cosmetically-acceptable ester (or CTG) to a vessel; adding and emulsifying wax to the vessel and mixing the ester, while heating to 70-75° C.; adding one or more polymers, where the polymer(s) have an aliphatic backbone and a plurality of pendant groups thereon that are pendant ionic or ionizable groups, or pendant groups having at least one permanent dipole that includes an acid, alcohol, thiol, ester, amine, amide, imide, imine, or nitrile moiety, or a polysachharide; reducing the temperature to 45-35° C.; pouring the final blend into a container.

Applications Examples

When mixed with an aqueous medium at a temperature not exceeding 30° C., the cold process formulation aid of the present invention forms a hydrogel or an emulsion. It is also possible to form an emulsion or hydrogel by adding the cold process formulation aid of the present invention at temperatures that do not exceed the melt point of the wax component of the cold process formulation aid or the melt point of the cold process formulation aid itself.

Mascaras

Certain embodiments of the present invention are directed to mascaras that enhance the volume or thickness of eyelashes. In particularly preferred embodiments, mascara compositions comprising the cold formulation processing aid of the present invention not only have long wear and curl, but also exhibit less clumping (i.e., on application and over time) and are easily removed (i.e., with water).

In addition to the cold process formulation aid of the present invention, the mascara compositions may contain one or more of (i) a self-emulsifying wax, (ii) a latex polymer, preferably copolymers of a (meth)acrylic acid and its esters or acrylates copolymers, (iii) film-forming polymers, water-soluble and/or oil-soluble, (iv) water-soluble thickening or gelling agents, and fibers.

Non-limiting examples of water-soluble, film-forming polymers include: polyacrylates and polymethacrylates; acrylates copolymers such as those sold by The Lubrizol Corp. under the tradename Avalure® AC and by Interpolymer under the Syntran® PC tradename (Syntran® PC 5208—Polyacrylate-15; Syntran® PC 5205/5227—Polyacrylate-15 (and) Polyacrylate-17; 3; Syntran® PC 5117—Polyacrylate-18 (and) Polyacrylate-19; Syntran® PC 5100 Polyacrylate 21 (and) Acrylates/Dimethylaminoethyl Methacrylate Copolymer; Syntran® PC 5400 Ammonium Acrylates); polyvinyl acetates; polyvinyl alcohols; cellulose derivatives (e.g., hydroxymethyl cellulose, sodium carboxymethylcellulose, ethyl cellulose, hydroxyethyl-cellulose, hydroxypropyl cellulose, and hydroxypropyl methylcellulose); cellulose acetate phthalate aqueous dispersion; polymers of chitin or chitosan; vinyl polymers, including vinyl pyrrolidone, polyvinylpyrrolidone (PVP) and copolymers of vinyl pyrrolidone and PVP (e.g., vinylpyrrolidone/acrylates/lauryl methacrylate copolymer, acrylates/$C_{1-2}$ succinates/hydroxyacrylates copolymer; PVP/DMAPA acrylates copolymer; copolymers of vinylpyrrolidone and caprolactam; polyurethanes (e.g., Polyurethane-1, a mixture of 30% polyurethane, 10% ethanol, and 60% water, sold under the tradename Luviset® P.U.R. by BASF, Aktiengesellschaft); polyester-polyurethane aqueous dispersions, such as those sold by The Lubrizol Corp. under the trade names Avalure® UR® and Sancure®; and quaternized polymers (e.g., Syntran® PC 5320—Polyquaternium sold by Interpolymer).

Non-limiting examples of oil-soluble, film-forming polymers include hydrogenated polyisobutenes, polydecenes, adipic acid/diethylene glycol/glycerin crosspolymer, polyethylene, polyvinyl laurate, dienes (in particular, polybutadiene and cylopentadiene), and synthetic-terpene based resins.

Water-soluble thickening or gelling agents may be film-forming polymers and include: polyacrylamides such as Sepigel 305 (INCI name: polyacrylamide/$C_{13-14}$ isoparaffin/Laureth 7) or Simulgel 600 (CTFA name: acrylamide/sodium acryloyldimethyltaurate copolymer/isohexadecane/polysorbate 80); polyvinylpyrrolidone (PVP); polyvinyl alcohol; crosslinked acrylates, such as crosslinked poly (2-ethylhexyl acrylate), and hydrophobically-modified acrylates; cellulose derivatives (illustrated above), polysaccharides and gums; and crosslinked methacryloyloxyethyl-trimethylammonium chloride homopolymers sold under the name Salcare SC95.

In preferred embodiments, the mascara contains both a water-soluble, film-forming polymer and an oil-soluble, film-forming polymer, where the water-soluble, film-forming polymer is present at a concentration of from 0.5% to 25%, preferably from 1% to 15%, still more preferably from 1% to 10%, and where the oil-soluble, film-forming polymer is present at a concentration of from 1% to 45%, preferably from 3% to 20%.

In mascara embodiments containing fibers, the fibers may be of natural origin (cotton, silk, wool) or synthetic (polyester, rayon, nylon or other polyamides). Fibers typically have an average length ranging from 0.5 mm to 4.0 mm, and preferably have an average length ranging from 1.5 mm to 2.5 mm. When present, fibers may comprise from 0.5% to 10% wt/wt, preferably from 1% to 5% wt/wt.

In other embodiments directed to volumizing hair fibers, in particular eyelashes, the composition may include particles, including powders of the present invention, that are initially at least about 5 microns in equivalent diameter or that prior to upon application to the lashes swell to a size of at least about 5 microns in equivalent diameter by any chemical or physical means.

One embodiment of the present invention is directed to volumizing eyelashes in a two-step process, first by applying a basecoat mascara followed by separate application of a topcoat mascara. The basecoat contains CPFAs of the present invention and is exemplified by the following formula: CPW-2 (Polyethylene, Sodium Polyacrylate)—10%; CPW-S (Sunflower wax, Sodium polyacrylate)—5%; Isodecane (40%); Mica 5%; CPW-5 (Polyethylene, Sodium Polyacrylate)—12%); Black Iron Oxide (8%); Jeelux VHIPP (Isopropyl Palmitate, Bis-vinyl Dimethicone/Dimethicone Copolymer)—25%. The topcoat is exemplified by the following formulation: Water—60%; PEG 150—5%; DC 200 1.5 cst (Dimethicone) 25%; Avalure® UR 450 (PPG-17/IPDI/DMPA copolymer)—10%.

Self-Tanners/Autobronzers

Self-tanning formulations containing cold process formulation aids of the present invention include dihydroxyacetone and at least one reducing sugar, preferably and preferably also include a high molecular weight cationic polymer, preferred examples of the latter being described in the following U.S. patents, the disclosures of which are incorporated, in pertinent part, by reference: U.S. Pat. Nos. 4,599,379; 4,628,078; 4,835,206; 4,849,484; and 5,100,660. Erythrulose a $C_4$-ketosugar (1,3,4-trihydroxy-butan-2-one) is a preferred reducing sugar and can be used in D- or L-form or also as the racemate. Other reducing sugars having self-tanning properties that can be used in combination with erythrulose include glucose, xylose, fructose, reose, ribose, arabinose, allose, tallose, altrose, mannose, galactose, lactose, sucrose, erythrose and glyceraldehyde.

Topical Anti-Aging and Dermatologic Compositions

Emulsions made with CPFAs of the present invention provide advantages over conventional emulsions made by heating two discontinuous phases and then mixing the two phases at elevated temperature until homogenous. Notably, temperature-sensitive active ingredients (those whose activity is negatively impacted, i.e., diminished, at elevated temperature and fragrances can be added directly to the cold process emulsion.

Emulsions containing CPFAs of the present invention can include a multitude of anti-aging skin care active ingredient. By "anti-aging skin care active ingredient" is meant an ingredient that helps to reduce the appearance of and/or prevent the formation of fine lines, wrinkles, age spots, sallowness, blotchiness, redness, dark circles (i.e., under the eyes). Anti-aging skin care active ingredients are also understood as helping to reduce skin oiliness, reduce transepidermal water loss, improve skin retention of moisture and/or improve skin elasticity. Non-limiting examples of skin care actives include: anti-inflammatory agents (e.g., 1,3 1,6 beta glucan; polyglutamic acid (and) polyfructose); humectants; skin bleaching/lightening agents (e.g., hydroquinone, kojic acid, ascorbic acid, magnesium ascorbyl phosphate, ascorbyl 3 aminopropyl phosphate, ascorbyl 3 aminopropyl dihydrogen phosphate); skin soothing agents (e.g., panthenol and derivatives, aloe vera, pantothenic acid and its derivatives, allantoin, bisabolol, and dipotassium glycyrrhizinate); anti-oxidants; vitamins and derivatives thereof; exfoliants (e.g., abrasive particles, hydroxy-acids); anti-aging ingredients, including short-chain peptides (e.g., having less than about 12 amino acids); and self-tanning agents (e.g., dihydroxyacetone).

Reduction in the appearance of fine lines and wrinkles can be measured by a number of techniques known to those of skill in the art and including clinical assessment by a trained observer (e.g., doctor, nurse, technician) instrumentally (e.g., by use of Silflo replica masks or an imaging system such as VISIA from Canfield Scientific.) Improvements in elasticity are measurable, for example, with a Twistometer. Reduction in the rate of transepidermal water loss and improvement in skin moisture content are measurable, respectively, with an evaporimeter and corneometer.

In embodiments of the present invention where the cold process formulating aid is used to form a topical composition applied to skin exhibiting visible signs of aging (including fine lines, wrinkles, skin laxity, uneven pigmentation), acne lesions, psoriasis, rosacea or an inflammatory dermatosis, the composition may also contain a natural or synthetic analog of vitamin A (i.e., a "retinoid") including geometric isomers and stereoisomers, and includes the following compounds: retinol; retinal; $C_2$-$C_{22}$ alkyl esters of retinol; including retinyl palmitate, retinyl acetate, retinyl propionate; retinoic acid (including all-trans retinoic acid and/or 13-cis-retinoic acid); as well as compounds described as retinoids in U.S. Pat. Nos. 4,677,120; 4,885,311; 5,049,584; and 5,124,356.

In addition to the cold process formulation aids of the present invention, cosmeceutical compositions that reduce the appearance of the visible signs of aging, topical compositions applied in the treatment of acne and other inflammatory dermatoses, as well as self-tanning compositions (described above), may contain hydroxy acids, alpha hydroxy acids (AHAs). As used in the present application, AHAs conform to the formula $(R_1)(R_2)C(OH)COOH$ where $R_1$ and $R_2$ may be the same or different, and are selected from the group consisting of H, F, C, Br, alkyl, aralkyl, or aryl having 1-29 carbon atoms. The alkyl, aryl or aralkyl groups may be straight, branched or cyclic. $R_1$ and $R_2$ may be further substituted with OH, CHO, COOH or a $C_{1-9}$ alkoxy group. Additionally, beta hydroxyacids and polyhydroxyacids may also be added to topical compositions according to the present invention.

Hair Care Products

Cold process emulsions or hydrogels formulated in accordance with the present invention include hair care actives known to those of skill in the art that moisturize, condition, improve bending modulus, increase tensile strength, increase sheen/shine, improve touchability, reduce split ends, volumize, reduce fly-away, and/or increase longevity of color treatment. Such materials include proteins and polypeptides and derivatives thereof, antioxidants, humectants and moisturizing and conditioning agents Antiperspirant/Deodorants; Wet Wipes In another embodiment, the CPFA of the present invention is advantageously employed in a process for making an extrudable antiperspirant/solid stick at temperatures below the melting point of the formula. In this process, a homogenized mixture of CPFA, an antiperspirant and/or deodorant ("AP/Deo") active ingredient (for example, a salt or complex of aluminum and/or zirconium), a structurant (e.g., fatty alcohols and other waxes), absorbent/drying agents (especially, talc, clay, starches), volatile silicone(s), and, optionally, one or more of suspending agents, emollients, and fragrance are mixed and homogenized to achieve a desired consistency and feel. The resulting mixture is extruded to obtain a uniform, solid, cohesive extrudate that is cut to a desired length.

The above process is further illustrated by the following non-limiting example formulation. The AP/Deo active ingredient is incorporated by premixing the active with water and possibly a small amount of propylene glycol. Absorbent/drying agents are particles 10 microns or less and are present in amount of from about 8 to 20% wt/wt. The volatile silicone(s) are present at a least 15% wt/wt. Transparent AP/Deo sticks can be achieved by forming an emulsion incorporating CPFAs of the present invention, particularly self-emulsifying CPFAs (e.g., those including one or more emulsifiers such as PEG-100 Stearate, Polysorbate-60, Glyceryl Stearate), and oil phase ingredients where the refractive indices of the oil and water phase are adjusted to within 0.0005 to 0.001 units at room temperature. PEG-400 glycol and PEGs having a molecular weight of greater than 400 can be used to make transparent/translucent gels, some of which are referred to in the art as "ringing" gels. Such PEGs can be used to make CPFAs of the present invention. For example, combining a PAD with PEG 400 Glycol will produce a clear transparent/translucent emulsion.

A natural deodorizing powder may be prepared by mixing alum, sodium bicarbonate, waxes of essential oil and CPFAs formed from natural waxes and sodium polyacrylate (or one or more salts of sodium polyacrylate or both).

Low-viscosity AP/Deo roll-ons or sprays (viscosity of less than about 2,500 mPas) can be formulated with self-emulsifying CPFAs of the present invention as defined in the preceding paragraph. A non-limiting example of such a low-viscosity AP/Deo composition contains CPFAs of the present invention at a concentration of from 1% to 10% wt/wt, two glucosides in a concentration of from 2% to 10% wt/wt, polyglycerol-2-dipolyhydroxystearate at a concentration of from 5% to 8% wt/wt, about 5% wt/wt of a polyol, with the balance of the composition being oil components selected from the group of linear hydrocarbons with a chain length of 8 to 40 carbon atoms, esters, particularly esters formed by the reaction of $C_6$-$C_{24}$ fatty acids with $C_6$-$C_{24}$ fatty alcohols, Guerbet alcohols based on $C_6$-$C_{18}$ fatty alcohols, and silicone compounds. The esters and linear hydrocarbons may be branched or unbranched, saturated or unsaturated. In addition to use as roll-ons, sprays, the above-described composition may be used as an impregnating liquid for wet wipes.

Transfer-Resistant Colored Makeup Compositions

In one embodiment, the present invention is directed to a process for limiting and/or preventing the transfer of a colored make-up composition from the lips or the skin, where the colored make-up composition is comprised of a CPFA of the present invention, at least partially crosslinked, elastomeric organopolysiloxane, a fatty phase containing at least one oil that is volatile at room temperature. Transfer resistant lipsticks preferably include a siloxysilicate polymer, preferably trimethylsiloxy silicate. The colored make-up composition may be in the form of a foundation, a blush, an eyeshadow, a concealer, a lipstick, a lipstick topcoat (i.e., applied over a base lipstick), and a tinted moisturizer, preferably containing UV radiation absorbers or blocks. Tests for transfer-resistance are known to those of skill in the art and include the "Kiss Test" described in Example 4 of U.S. Pat. No. 5,505,937.

Additional Cosmetic Ingredients

As will be appreciated by persons skill in the art, a wide-range of water-immiscible materials may be added to the cold process emulsions of the present invention, non-limiting examples of which include (i) non-volatile silicone fluids, preferably have a viscosity ranging of from about 20 to 100,000 centistokes at 25° C.; (ii) nonvolatile hydrocarbon oils including, but not limited to, isoparaffins and olefins having greater than 20 carbon atoms; (iii) cosmetically-acceptable esters (as defined below); (iv) lanolin and derivatives thereof; (v) glyceryl esters of fatty acids or triglycerides, derived from animal or vegetable sources; (vi) fluorinated oils including, but not limited to, fluorinated silicones, fluorinated esters and perfluoropolyethers; and (vii) Guerbet esters formed by the reaction of a carboxylic acid with a Guerbet alcohol.

As used herein, "cosmetically-acceptable ester" refers to compounds formed by the reaction of a mono-, di- or tri-carboxylic acid with an aliphatic or aromatic alcohol that are not irritating or sensitizing when applied to the skin. The carboxylic acid may contain from 2 to 30 carbon atoms, and may be straight-chain or branched-chain, saturated or unsaturated. The carboxylic acid may also be substituted with one or more hydroxyl groups. The aliphatic or aromatic alcohol may contain 2 to 30 carbon atoms, may be straight-chain or branched-chain, saturated or unsaturated. The aliphatic or aromatic alcohol may contain one or more substituents including, for example, a hydroxyl group.

Among other things, the above-listed water-immiscible materials may provide emolliency. Other emollients known in the art may be used, including urethane emollients and conditioners sold under the tradename Polyderm by Alzo International, non-limiting examples of the latter including Polyderm PPI—CO-40 (PEG-40 Hydrogenated Castor Oil/IPDI Copolymer) and Polyderm PPI-SI (Dimethiconol/IPDI Copolymer).

By structuring agent is meant an ingredient that improves or increases the hardness of an oil as measured by test methods well-known to those of skill in the art including drop point and penetration.

One or more plasticizers may be added to compositions of the present invention to further modify spreadability and other application characteristics of the composition. Plasticizers may be present at concentrations of from about 0.01% to about 20%, preferably about 0.05% to about 15%, and more preferably from about 0.1% to about 10%.

Cold process emulsions according to the present invention may contain one or more surfactants at a concentration of from about 0.01% to about 20%, preferably from about 0.1% to about 15%, and more preferably from about 0.5% to about 10% by weight of the total composition. The surfactants may be amphoteric, anionic, cationic, or non-ionic.

Amphoteric surfactants suitable for use in compositions of the present invention include propionates, alkyldimethyl betaines, alkylamido betaines, sulfobetaines, imidazoline.

Anionic surfactants suitable for use in compositions of the present invention include fatty alcohol sulfates, alpha olefin sulfonates, sulfosuccinates, phosphate esters, carboxylates and sarcosinates.

Cationic surfactants suitable for use in compositions of the present invention include alkyl quaternaries, alylamido quaternaries, imidazoline quaternaries.

Nonionic ionic surfactants suitable for use in compositions of the present invention include alkanolamides, ethoxylated amides, esters, alkoxylated alcohols, alkoxylated triglycerides, alkylpolyglucosides, amine oxides, sorbitan esters and ethoxylates.

Surfactants may also be silicone surfactants including, but not limited, dimethicone copolyols, alkyl dimethicone copolyols, silicone quaternary compounds, silicone phosphate esters and silicone esters.

Encapsulates

The cold processing formulation aids of the present invention may contain other materials embedded therein. Encapsulation may be achieved by mixing other materials with the required components of the cold processing aid of the present invention as taught herein. In one example, the other material(s) are mixed with the cold processing aid of the present invention in a molten state, before it is atomized and cooled to create a solid wax particle. Non-limiting examples of materials that can be embedded inside the cold processing formulation aids of the present invention include, but are not limited to, pigments, preservatives, fillers, active ingredients (either hydrophilic or lipophilic), polymers, fragrance ingredients (e.g., essential oils and aroma-producing chemicals of natural or synthetic origin), and mixtures thereof.

Oil-in-Water Emulsions Containing High Molecular Weight Polysaccharides

In another embodiment, the CPFA described herein is used in oil-in-water emulsions that are stabilized with polysaccharides, especially xanthan, a poly(glucomannan), or both.

U.S. Pat. No. 6,831,107 discloses that high molecular weight polysaccharides stabilize oil-in-water emulsions (O/W), without increasing the low-shear viscosity of the emulsion, and allows lower levels of emulsifiers to be used. However, this patent also discloses that use of anionic materials, e.g. anionic surfactants, in combination with high molecular weight polysaccharides is highly disfavored because, among other reasons, the ionic material impairs the ability of the polysaccharide to stabilize the emulsion. Applicants have surprisingly discovered that, despite the fact that the CPFAs of the present invention include polymers having ionic or ionizable groups, the CPFAs are useful in oil-in-water emulsions that are stabilized with high molecular weight polysaccharides. When a CPFA of the type described herein is used, high temperature is not required to form the emulsion, provided that sufficient shear energy is supplied.

For example the CPFA can be incorporated at low temperature to provide rheology modification when higher viscosity products are desired. Emulsions made with CPFAs can be used as such in a personal care product, or they can be used to make articles, e.g. pads impregnated with such a product.

Non-limiting examples of rheology modifiers that can be incorporated in CPFAs of the present invention include: polyurethanes, acrylic polymers (as described above), latex, styrene/butadiene; polyvinyl alcohol; clays, including attapulgite, bentonite (both flocculating and non-flocculating), and other montmorillonite clays; cellulosic polymers as mentioned above, including carboxymethylcellulose, hydroxymethylcellulose, hydroxypropylmethylcellulose; sulfonates and salts thereof; gums (as described above), including but not limited to, guar, xanthan, cellulose, locust bean, and acacia; saccharides (as described above); proteins, including cassein, collagen, and albumin. All of the above rheology modifiers are preferably incorporated in the CPFAs of the present invention at concentrations of from about 0.2% to 2.0%.

In preferred embodiments of this aspect of the invention, a CPFA, an emulsifier, and emulsion stabilizer (polysachamide) are blended to provide a dry product that can be dispersed in water and readily then made into emulsions at low temperature. In these embodiments, it can be useful to use both high HLB and low HLB emulsifiers and optionally to include materials such as milling aids. Products according to this embodiment can be made by dry blending xanthan and polyglucomannan, emulsifiers and the CPFA and consolidating the blend, e.g. by extrusion, desirably at a temperature, sufficient that one or more of the components (typically one or more of the emulsifiers are at least partly melted and can so coat and/or bind the powder components especially the polysaccharides), to form pellets and then milling the pellets to a desired particle size. While less preferable with respect to energy/heat consumption, the use of CPFAs to thicken an O/W emulsion as described in this embodiment may also be useful in conventional heated emulsion processes.

A typical composition for such a dry blend, in parts by weight, is as follows: xanthan (3 to 8% wt/wt); polyglucomannan (3 to % 8 wt/wt); olive wax 84 to 94% wt/wt. The ratio of xanthan to polyglucomannan can be between 1:2 to 2:1.

Surface Coatings/Protectants

In addition to personal care applications, where compositions of the present invention containing CPFAs are applied to mammalian hair or skin, compositions containing CPFAs of the present invention may be applied as a protectant, moisturizer, sealer, to household, industrial, hospital and commercial hard surfaces as well as to the exterior surfaces of automotive and marine vehicles, including tires and wheels, recreational sports equipment, woven and nonwoven fabrics. Protectant, moisturizer and/or sealer formulations within the scope of the present invention may be applied for example, to rubber, vinyl, plastic, leather, fabric, carpeting.

As used in the present application, by "protectant" is meant a consumer or industrial product, preferably a spray, that coats the surface to minimize the degradation of the coated material due to environmental factors and provide a durable and shiny appearance. The protectant spray may, and in certain embodiments does contain, either or both of (i) a UV absorbing or reflecting/scattering compound known in the art and/or (ii) a cleansing agent (e.g., a surfactant). In embodiments directed to cleansing agents, positively charged "dirt particles" are entrained in the aqueous phase of an emulsion containing the CPFA of the present invention. Dirt is repelled from the surface while the wax within the emulsion attaches to the "uncharged", now clean surface.

CPFAs of the present invention may also be used in furniture restoration, i.e., to fill cracks.

Topical Hydro-Alcoholic Antiseptic

A topically-applied, hydro-alcoholic antiseptic product, meeting the criteria of the Tentative Final Monograph for OTC Healthcare Antiseptic Drug Products (Jun. 17, 1994), is illustrated below:

OTC Antiseptic Example 1

Phase A—Distilled Water (24%); Ethanol (70%)
Phase B—Cold Processing Aid of Present Invention (6%) (Sunflower Wax, Polyacrylate Crosspolymer-6, sold under the tradename CPW S-ZEN by Jeen International)

OTC Antiseptic Example 2

Phase A—Distilled Water (26%); Ethanol (65%); Amino Methyl Propanediol (1.0%); Glycerin 99.7% USP (3.0%)
Phase B—Cold Processing Aid of Present Invention (5%) (Sunflower Wax, Acrylates/$C_{10-30}$ Alkyl Acrylate Crosspolymer, sold under the tradename CPW-SUN21 by Jeen International)

The above OTC antiseptic product is prepared using a cold process formulation aid of the present invention by mixing at room temperature the ingredients of Phase A and Phase B separately, and then adding Phase B to Phase A. Consistent with the above Tentative Final OTC Monograph, the level of alcohol in this product may be adjusted to between 60 and 95%. Each of the above formulation are non-drying and leave a silky after feel.

Biomaterials

Cold process formulation aids of the present invention may be used in the manufacture of biocompatible materials, including, but not limited to, fillings, coatings, implants and "scaffolding" (i.e., to provide temporary support and stability for damaged tissue and/or to provide a substrate for growth of bone or tissue). The CPFA may include one or more crosslinked or photocurable (e.g., by ultraviolet light) functional groups. In one preferred embodiment, the CPFA biomaterial contains a polysaccharide backbone, for example, chitosan as disclosed in U.S. Pat. No. 7,914,819.

Ceramics and Concrete

Cold process formulation aids of the present invention may be incorporated into concrete and ceramics, thereby internally sealing the concrete or ceramic body composition with wax beads. For ceramics made by a dry grinding process, a substantially dry, ceramic raw batch (also known as a ceramic body composition) in a loose pulverant state (e.g., containing about 1% uncombined water with not more than 6% organic material) is admixed with a wax-water emulsion formed with one or more cold process formulation aids of the present invention. The slurry is screened and spray dried to create a flowable mass of small globules of wax-bonded ceramic. The resulting wax-bonded ceramic material is molded to form desired shapes that are then fired. Manufacturing methods based on admixing the cold process formulation aid of the present invention into the ceramic raw batch are advantageous because they allow for shaping of finished tiles, dinnerware or other ceramic articles without relying on the inherent plasticity of the ceramic body composition. Alternatively, cold process formulation aids of the present invention may be added to a ceramic raw batch slurry in a wet grinding process. The slurry is filtered, dried and fired.

Compositions for Decorative Application to a Surface

In other embodiments, the cold process formulation aid of the present invention ("CPFA") can be used in the manufacture of compositions, especially colored compositions, to be applied to decorate a surface, for example crayons, water colors, and water-based inks and paints.

In crayon embodiments, the CPFA may be at varying concentrations (e.g., 10%, 50%, or 75%) with a conventional crayon wax such as candle wax, and a pigment (typically 3% to 20%, by weight, of the total composition).

The combination is heated until it melts into a homogeneous liquid (about 40° C.). The mixture is then heated to about 82° C. The liquid combination is poured into a preheated mold of crayon-shaped holes. Water (at about 13° C.) is used to cool the mold, forming crayons in from 3 to 9 minutes. Use of the CPFA of the present invention provides for improved dispersion of the pigment and smoother transfer of the crayon composition to the surface to be decorated.

The CPFA of the present invention is advantageously used in formulating gum-arabic based water color paints to provide an improved more stable dispersion of the dye or pigment, and an improved smoothness and texture when the water color is applied to the surface to be decorated. Use of the CPFA of the present invention allows the water color paint to be made at low temperature, especially at or about room temperature, allowing even heat sensitive dyes of pigments to be used in the water color.

As a non-limiting example, a water color paint is made by combining water, gum arabic, pigment, optionally glycerin and/or PEG, and CPFA (at 2% to 10% by weight) at a temperature not exceeding 35° C. When cooled to room temperature, the water color has a smooth, easy flowing texture, and can be applied with a minimum of drip or run.

A typical base (vehicle) for water color formulation formulation is as follows: 80% water soluble, waxy polyethylene glycol, 4% stearyl alcohol, 6% polyhydric alcohol, 5% water by volume, and 5% by weight of CPFA. The base can be combined with the desired amount of pigment. The vehicle is particularly useful with cobalt violet, viridian or cadmium red that tend to separate from the vehicle.

In ink embodiments, the CPFA of the present invention is used as a flatting agent in conventional ink formulations to improve the surface properties of the known ink or paint formulations.

As a non-limiting example of a printing ink within the scope of the present invention, a CPFA may be added to the ink formulation in an amount of from about 3% to about 14%, based on the total weight of the formulation. Use of the CPFA of the present invention allows the ink to be formulated at relatively low temperature. Use of the CPFA of the present invention improves, among other things, bleed and rub-resistance of the ink.

In a water-based paint, the CPFA of the present invention may be used at about 1% to about 6%, based on the total weight of the paint. Inclusion of the CPFA of the present invention reduces gloss and improves the scratch and "black heel" resistance of the dry paint.

Internal sealing of concrete or ceramic tiles with cold processing formulating aids of the present invention is further illustrated by the following example. A portion of a wet (i.e., pourable) concrete mix is replaced with a cold process formulation aid of the present invention, in the form of a powder. The powder is mixed with other components of the concrete until it is well dispersed. The concrete is then cured. After the desired strength is achieved, the concrete is heated; this causes the powder to melt and flow into capillaries and pores of the concrete. By way of further example, a concrete bridge deck having a depth of three inches and conforming to standards promulgated by the Federal Highway Administration is made by replacing about 8% of a concrete mix with a cold processing aid of the present invention and heating the resulting mixture for approximately 5 to 9 hours.

Cold Process Emulsion Formed from Dual-Chambered Dispenser or Kit

A cold process formulation aid of the present invention, either in powder or paste, is stored in one side of dual-chambered container. On the other side of the container is separately stored an aqueous medium. The aqueous medium and cold process formulation aid are co-dispensed, forming an emulsion or hydrogel.

A cold process formulation aid of the present invention is admixed with an aqueous medium forming an aqueous base, which is then stored in one side of dual-chambered container. On the other side of the container is separately stored a combination of non-aqueous ingredients (e.g., an oil phase). The aqueous base and oil phase are co-dispensed, forming an emulsion or hydrogel.

A kit is provided to a user comprising (i) a cold process formulation aid of the present invention product in the form of a powder (e.g., in an sealed aluminum sachet) and (ii) an aqueous medium and/or (iii) an oil phase. The user is instructed to combine the powder with the aqueous medium or to combine distilled or tap water with the powder. The user is then further instructed to add the oil phase, thereby creating an emulsion of hydrogel.

Broad-Spectrum, Highly SPF Retaining Photoprotective Composition

One aspect of the present invention is directed to a broad-spectrum photoprotective composition that retains a high percentage of the labeled SPF.

By "highly SPF retaining" is meant that the photoprotective composition (e.g., sunscreen per se, or moisturizer contain sunscreen ingredients) retains at least 90% of its labeled SPF after irradiation for an ultraviolet radiation source producing from 2-6 minimal erythemal doses (42-36 mJ/cm$^2$).

As used in the present application, a photoprotective composition provides "broad-spectrum" photoprotection if it meets the requirements for labeling an over-the-counter (OTC) sunscreen drug product as "broad spectrum", under the FDA's Final 2012 Sunscreen Monograph entitled "Labeling and Effectiveness Testing; Sunscreen Drug Products for Over-the-Counter Human Use" promulgated by the Food and Drug Administration (FDA) on Jun. 17, 2011. See 76 FR 35620 et seq. More particularly, a photoprotective composition according to the present invention has a critical wavelength of at least 370 nm, where critical wavelength is the wavelength at which the integral of the spectral absorbance curve reaches 90 percent of the integral over the UV spectrum from 290 to 400 nm, and, accordingly, provides "broad-spectrum" protection from UV light across the terrestrial UV spectrum.

The broad-spectrum nature of a photoprotective product containing CPFAs of the present invention is confirmed using optical-grade polymethyl-methacrylate (PMMA) plates, a solar simulator, and a spectrometer, each as described below.

PMMA plates are rectangular substrates for measuring sunscreen absorbance spectra. They have an area of at least 16 square centimeters (with no side shorter than 4 cm), and are "roughened" on one side to emulate the surface topography of human skin—expressed as a surface topography measure (Sa) of between 2 and 7 micrometers. Commercially available PMMA plates suitable for use in measuring sunscreen absorbance spectra, and thus determining whether a sunscreen is broad spectrum and/or photostable, include the Schönberg sandblasted plate (Schonberg GmbH & Co KG; Hamburg, Germany), the Helioscreen HD-6 molded plate, (Helioscreen; Creil, France), and the "Skin-Mimicking" Substrate (Shiseido; Yokohama, Japan) as described in Miura et al., *Photochem. Photobiol.* 88: 475-482 (2012).

The solar simulator is a light source known in the art that produces a continuous spectral distribution of UV radiation from 290 to 400 nanometers, and has a particular erythema-effective radiation contribution in the following wavelengths ranges: less than 290 nm: less than 0.1%; from 290 to 300 nm: 1.0 to 8.0%; from 290 to 310 nm: 49.0% to 65.0%; from 290 to 320 nm: 85.0-90.0%; from 290 to 330 nm: 91.5 to 95.5%; from 290 to 340 nm: 94.0 to 97.0%; from 290 to 400 nm: 99.9 to 100.0%. Calculation of erythema action spectrum is set out at 21 CFR § 201.327(i)(1)(ii).

The spectrometer is calibrated to accurately measure transmittance through the photoprotective composition being tested over the range of terrestrial solar UV wavelengths (290 to 400 nm). More particularly, the spectrometer has input slits that provide a bandwidth that is less than or equal to 1 nm. A spectrometer with or without an integrating sphere may be used. If the spectrometer is not equipped with an integrating sphere, an ultraviolet radiation diffuser constructed from any UV radiation transparent material (e.g., Teflon® or quartz) is placed between the sunscreen sample and the input optics of the spectrometer.

A specified amount of a test product is uniformly distributed over the roughened side of the PMMA plate. The product being tested is applied in series of small dots over the entire PMMA plate, and then spread evenly using a gloved finger. Spreading is done with a very light spreading action for approximately 30 seconds, followed by spreading with greater pressure for approximately 30 seconds.

Each plate is placed in a horizontal position (to avoid flowing of the sunscreen from one edge of the plate to the other) on the upper surface of a sample holder—a thin, flat plate with a suitable aperture through which UV radiation can pass—with the roughened side facing. The PMMA plate is mounted as close as possible to the input optics of the spectrometer to maximize capture of forward scattered radiation. The plate treated with the applied test product is first allowed to equilibrate for 15 minutes in the dark, and then undergoes a "pre-irradiation" step in which the sample is exposed to an erythemal effective dose of 800 J/m$^2$ (equivalent to 4 MEDs). Next, transmittance values are measured and recorded at each wavelength (i.e., at 1 nanometer intervals) over the entire UV spectrum (290 to 400 nanometers). At least five transmittance measurements are taken of the sunscreen product of the present invention ("P") are taken at five different locations on the PMMA plate—P1(λ), P2(λ), P3(λ), P4(λ), and P5(λ). An equal number of transmittance measurements are taken of a control ("C"), PMMA plates coated with 15 microliters of glycerin, with no sunscreen product—C1(λ), C2(λ), C3(λ), C4(λ), and C5(λ).

The mean transmittance for each wavelength, is the ratio of the mean of the C(λ) values to the mean of the P(λ) values. Mean transmittance values, are converted into mean absorbance values, at each wavelength by taking the negative logarithm of the mean transmittance value. The above calculations yield 111 monochromatic absorbance values in 1-nanometer increments from 290 to 400 nanometers.

Another aspect of the present invention is directed to photoprotective compositions containing a CPFA comprising a benzone—specifically Dioxybenzone (also known as Benzophenone-8) Oxybenzone (also known as Benzophenone-3, Eusolex 4360, Escalol 567) Sulisobenzone (also known as 2-Hydroxy-4-Methoxybenzophenone-5-sulfonic acid, 3-Benzoyl-4-hydroxy-6-methoxybenzenesulfonic acid, Benzophenone-4, Escalol 577) or dibenzoylmethane derivative selected from the group consisting of 2-methyl-dibenzoylmethane; 4-methyldibenzoylmethane; 4-isopropyl-dibenzoylmethane; 4-tert-butyldibenzoylmethane (also known as Avobenzone, Parsol® 1789, Eusolex 9020); 2,4-dimethyldibenzoylmethane; 2,5-dimethyldibenzoylmethane; 4-tert-butyl-4'-methoxy-dibenzoylmethane; 4,4'-diisopropyl-dibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; and 2,6-dimethyl-4-tert-butyl-4'-methoxy-dibenzoylmethane.

Formulation Example 1: CPW-EW1LP/CPW-2 Lotion (J2-56)

| | | | | |
|---|---|---|---|---|
| A | DI Water | Distilled water | | 81.0 |
| A | Jeesperse ® CPW-EW1LP | Stearic Acid, Ceteareth-20, Cetyl Stearyl Alcohol, Sodium Polyacrylate | Jeen Int'l | 7.0 |
| A | Jeesperse ® CPW-2 | Polyethylene, Sodium Polyacrylate | Jeen Int'l | 2.0 |
| A | Triethanolamine 99% | Triethanolamine | Jeen Int'l | 1.0 |
| B | Mineral Oil | Mineral Oil | Carnation | 2.0 |
| B | Jeechem ® IPM | Isopropyl Myristate | Jeen Int'l | 2.0 |
| B | Jeesilc ® PDS-350 | Dimethicone | Jeen Int'l | 2.0 |
| B | Glycerine 99% | Glycerine | Jeen Int'l | 1.0 |
| B | Vitamin E USP | DL-Alpha Tocopheryl Acetate | Jeen Int'l | 0.4 |
| B | Creamy Peach Fragrance | Fragrance | Lenoci | 0.1 |
| B | Safflower Oil | *Carthamus Tinctorius* (Safflower) Seed Oil | Jeen Int'l | 0.5 |
| B | Jeecide ® G-II | Propylene Glycol, Diazolidinyl Urea, Methyl Paraben, Propyl Paraben | Jeen Int'l | 1.0 |

Add all ingredients from Phase A and mix until uniform. Add Phase B ingredients, one at the time and mix well until homogenous.

Formulation Example 2: CPW-EW-1 LP/CPW-2 Sunscreen (J2-60)

| | | | | |
|---|---|---|---|---|
| A | DI Water | Distilled Water | | 66.7 |
| A | AMPD | Amino Methyl Propanediol | Angus | 0.7 |
| A | Jeesperse CPW-EW1 LP | Stearic Acid, Ceteareth-20, Cetearyl Alcohol, Sodium Polyacrylate | Jeen Int'l | 7.0 |
| A | Jeesperse ® CPW-2 | Polyethylene, Sodium Polyacrylate | Jeen Int'l | 2.0 |
| B | Glycerin 99.7% USP | Glycerin | Jeen Int'l | 2.0 |
| B | Cherry Vanilla Fragrance | Fragrance | Lenoci | 0.1 |
| B | Vitamin E USP | Dl-Alpha Tocopheryl Acetate | Jeen Int'l | 0.5 |
| B | Jeecide ® G-II | Propylene Glycol, Diazolidinyl Urea, Methyl Paraben, Propyl Paraben | Jeen Int'l | 1.0 |
| C | Sunscreen Blend* | | Jeen Int'l | 20.0 |

Combine DI Water with AMPD and mix until uniform. Add Jeesperse's one at the time and mix until homogenous. Add phase B and C ingredients and mix until uniform.

*The following FDA-approved sunscreens and sunblocks may be used in sunscreen blend: p-Aminobenzoic acid up to 15%; Avobenzone up to 3%; Cinoxate up to 3%; Dioxybenzone up to 3%; Homosalate up to 15%; Menthyl anthranilate up to 5%; Octocrylene up to 10%; Octylmethoxycinnamate (Octinoxate) up to 7.5%; Octyl salicylate up to 5%; Oxybenzone up to 6%; Padimate O up to 8%; Phenylbenzimidazole sulfonic acid (Ensulizole) up to 4%; Sulisobenzone up to 10%; Titanium dioxide up to 25%; Trolamine salicylate up to 12%; Zinc oxide up to 25%. FDA regulations known to those of skill in the art further describe permitted ingredient combinations. Other sunscreens and sunblocks are approved in countries outside the US and are suitable for inclusion in compositions of the present invention.

Formulation Example 3: CPW-CG-T Tanning Lotion (J2-85 MC)

| | | | | |
|---|---|---|---|---|
| A | Deionized Water | Water | | 78.0 |
| A | Jeesperse CPW-CG-T | Cetyl Alcohol, Sodium Acrylate/Sodium Acryloyl Dimethyl Taurate Copolymer, Glyceryl Stearate, Caprylic/Capric Triglyceride | Jeen Int'l | 5.0 |
| B | Dihydroxyacetone | Dihydroxyacetone | EMD Chemical | 3.0 |
| B | Coconut Oil | Cocos Nucifera (Coconut) Oil | Jeen Int'l | 2.0 |
| B | Jeesorb L-20NF | Polysorbate 20 | Jeen Int'l | 1.0 |
| B | Jeechem IPM | Isopropyl Myristate | Jeen Int'l | 5.0 |
| B | Jeechem ® BUGL | Butylene Glycol | Jeen Int'l | 2.0 |
| B | Jeesilc ® 35C | Dimethicone, Dimethicone Crosspolymer-3 | Jeen Int'l | 3.0 |
| B | Jeecide ® GII | Propylene Glycol, Diazolidinyl Urea, Methyl Paraben, Propyl Paraben | Jeen Int'l | 1.0 |

Mix Phase A at room temperature. Add Phase B and mix until homogenous.

Formulation Example 4: CPW-GCS Body Lotion (J7/51 A& B)

| | | | | | |
|---|---|---|---|---|---|
| A | DI Water | Distilled Water | | 72.30 | 77.30 |
| A | Glycerin 99 | Glycerin | Jeen Int'l | 4.00 | 4.00 |
| A | TEA 99 | Triethanolamine | Jeen Int'l | 0.70 | 0.70 |
| B | Jeesperse ® CPW-GCS | Stearic Acid, Cetearyl Alcohol, Glyceryl Stearate, PEG-100 Stearate, Sodium Polyacrylate | Jeen Int'l | 8.00 | 8.00 |
| C | Mineral Oil | Mineral Oil | Carnation | 8.00 | 5.00 |
| C | Jeesilc ® PDS-100 | Dimethicone | Jeen Int'l | 4.00 | 2.00 |
| D | Jeecide ® G II | Diazolidinyl Urea & Methylparaben & Propylparaben & Propylene Glycol | Jeen Int'l | 1.00 | 1.00 |
| D | Fragrance | Fragrance | | 2.00 | 2.00 |

Add D.I. Water, glycerin and the TEA. Mix until uniform using low speed homogenizing agitation. Sprinkle in Phase B ingredient and mix until the batch is smooth. Add Phase C ingredients one at a time to the batch and mix well using slow speed homogenization. Ad Phase D ingredients one at a time and mix with low speed homogenizing agitation.

Formulation Example 5: CPW-2+Jeesilc® 6056 (J8-23A)

| | | | | |
|---|---|---|---|---|
| A | Jeesperse ® CPW-2 | Polyethylene, Sodium Polyacrylate | Jeen Int'l | 5.00 |
| A | DI Water | Distilled Water | | 89.0 |
| A | Jeecide ® CAP-5 | Phenoxyethanol, Caprylyl Glycol, Potassium Sorbate, Water, Hexylene Glycol | Jeen Int'l | 1.00 |
| B | Jeesilc ® 6056 | Dimethicone, Dimethiconol, Laureth-4, Laureth-23 | Jeen Int'l | 5.00 |

Combine Phase A. Combine Phase B. Combine Phase A and Phase B and mix until homogenous.

Formulation Example 6: CPW-S Hydrogel Paint (J8-46)

| | | | | |
|---|---|---|---|---|
| A | Water | Water | | 60.6 |
| A | Shea Butter | Shea (Butyrospermum Parkii) Butter | Jeen Int'l | 5.00 |
| A | Cocoa Butter USP Deodorized | Theobroma Cacao (Cocoa) Seed Butter | Jeen Int'l | 2.00 |
| A | Coconut Oil | Cocos Nucifera (Coconut) Oil | Jeen Int'l | 5.00 |
| A | Jeechem ® CTG | Caprylic/Capric Triglyceride | Jeen Int'l | 5.00 |
| A | Jeecide ® CAP-5 | Phenoxyethanol, Caprylyl Glycol, Potassium Sorbate, Water, Hexylene Glycol | Jeen Int'l | 0.80 |
| A | Jeesilc ® EM-90 | Cetyl Peg/Ppg-10 Dimethicone | Jeen Int'l | 2.00 |
| A | Performa V 825 | Synthetic Wax | Presperse | 2.50 |
| B | Jeesperse ® CPW-S | Sunflower Wax, Sodium Polyacrylate | Jeen Int'l | 4.00 |
| C | SW40R7C | Red 7 | Kobo | 6.50 |
| C | SW60ER | Red Oxide | Kobo | 0.80 |
| C | SW55EB | Black Oxide | Kobo | 0.20 |
| C | Mica | Mica | Kobo | 2.60 |
| C | KTZ Ultrashimmer | Mica And TiO$_2$ | Kobo | 3.00 |

Mix and heat Phase A to 70-75'C. Add Phase B mix until homogenous. Add Phase C mix until homogenous. Mix while cooking to room temperature.

Formulation Example 7: CPW Hydrogen Peroxide (J8-62/62A)

| | | | | | |
|---|---|---|---|---|---|
| A | Hydrogen Peroxide | Hydrogen Peroxide (3% Solution) | | 90 | 90 |
| B | Jeesperse CPW-3 | Polyethylene, Sodium Polyacrylate | Jeen Int'l | 0 | 10 |

Add Phase B to Phase A while mixing. Mix until homogenous.

Formulation Example 8: CPW-S Hydrogel Paint (J9-67)

| | | | | |
|---|---|---|---|---|
| A | Water | Water | | 59.3 |
| A | Shea Butter | Shea (Butyrospermum Parkii) Butter | Jeen Int'l | 5.00 |
| A | Cocoa Butter USP Deodorized | Theobroma Cacao (Cocoa) Seed Butter | Jeen Int' | 2.00 |
| A | Coconut Oil | Cocos Nucifera (Coconut) Oil | Jeen Intl | 5.00 |
| A | Jeechem ® CTG | Caprylic/Capric Triglyceride | Jeen Int'l | 5.00 |
| A | Jeecide ® CAP-5 | Phenoxyethanol, Caprylyl Glycol, Potassium Sorbate, Water, Hexylene Glycol | Jeen Int'l | 0.80 |
| A | Jeesilc ® EM-90 | Cetyl Peg/Ppg-10 Dimethicone | Jeen Int'l | 2.00 |
| A | Performa V 825 | Synthetic Wax | Presperse | 2.50 |
| B | Jeesperse ® CPW-S | Sunflower Wax, Sodium Polyacrylate | Jeen Int'l | 4.00 |
| C | SW40R7C | Red 7 | Kobo | 1.00 |
| C | SW60ER | Red Oxide | Kobo | 5.00 |

| | | | | |
|---|---|---|---|---|
| C | SW55EB | Black Oxide | Kobo | 1.40 |
| C | Mica | Mica | Kobo | 3.00 |
| C | KTZ Copper | Mica And Iron Oxide | Kobo | 3.00 |
| C | Superb Silver | Mica And Titanium Dioxide | Kobo | 1.00 |

Mix and heat Phase A to 70-75'C. Add Phase B mix until homogenous. Add Phase C mix until homogenous. Mix while cooking to room temperature.

Formulation Example 9: CPW-DG ST1 (J8-79)

| | | | | |
|---|---|---|---|---|
| A | Water | Water | | 70.0 |
| A | Jeesperse ® CPW-DG ST1 | Titanium Dioxide, Polyethylene, Caprylic/Capric Triglyceride, Sodium Polyacrylate, Yellow Iron Oxide, Red Iron Oxide, Black Iron Oxide | Jeen Int'l | 18.0 |
| B | Jeechem ® ISNP | Isostearyl Neopentanoate | Jeen Int'l | 4.00 |
| B | Jeesilc ® PDS 5 | Dimethicone | Jeen Int'l | 3.50 |
| B | Jeecide ® CAP-5 | Phenoxyethanol, Caprylyl Glycol, PotassiumSorbate, Water, Hexylene Glycol | Jeen Int'l | 1.00 |
| C | Mica | Mica | Kobo | 2.6 |
| C | BPD-500 | Trimethyl Hexylactone Crosspolymer (and) Silica | Kobo | 0.90 |

Mix Phase A. Mix Phase B until homogenous. Add Phase B to Phase A mix until homogenous. Add Phase C mix until homogenous.

Formulation Example 10: CPW-S Mascara J8-87/J8-88 CPW-S J8-87 Base

| | | | | |
|---|---|---|---|---|
| A | Water | Water | | 89.0 |
| A | Jeesperse ® CPW-S | *Helianthuss Annuus* (Sunflower) Seed Wax, Sodium Polyacrylate | Jeen Int'l | 10.0 |
| B | Jeecide ® CAP-5 | Phenoxyethanol, Caprylyl Glycol, Potassium Sorbate, Water, Hexylene Glycol | Jeen Int'l | 1.00 |

Formulation Example 11: CPW-S Mascara (J8-87 and J8-88)

| | | | | | |
|---|---|---|---|---|---|
| A | Jeesperse ® CPW-S J8-87 Base | Water, Jeesperse CPW-S Jeecide ® CAP-5 | Jeen Int'l | 60.3 | 71.1 |
| B | LUVISET PUR | Water, Polyurethane, Ethanol | BASF | 30.7 | — |
| B | FA 4002 ID | Isododecane, Silicone Acrylate | Dow Corning | — | 17.4 |
| B | Jeesilc ® EM-90 | Cetyl PEG/PPG-10 Dimethicone | Jeen Int'l | — | 1.00 |
| C | Black Oxide 11J2 | Iron Oxide (77499), Triethoxycaprylyl Silane | Kobo | 9.00 | 10.5 |

Mix Phase A until homogenous. Add in Phase B and mix. Add in Phase C and mix.

Formulation Example 12: CPW-3 Velvet Primer (J9-52A NJM)

| | | | | |
|---|---|---|---|---|
| A | DI Water | Distilled water | | 75.0 |
| A | Jeesperse ® CPW-3 | Polyethylene, Sodium Polyacrylate | Jeen Int'l | 6.0 |
| B | Jeelux ® D2T | Isohexadecane, Dimethicone, Triisosteryl Citrate, Bis-Vinyl Dimethicone/Dimethicone Copolymer | Jeen Int'l | 5.0 |
| B | Jeesilc ® EM-90 | Cetyl PEG/PPG-10 Dimethicone | Jeen Int'l | 2.0 |
| B | Jeesilc ® DS-8 | PEG-8 Dimethicone | Jeen Int'l | 1.0 |
| B | Jeechem ® CTG | Caprylic/Capric Triglyceride | Jeen Int'l | 10.0 |
| B | Jeecide ® CAP-5 | Phenoxyethanol, Caprylyl Glycol, Potassium Sorbate, Water, Hexylene Glycol | Jeen Int'l | 1.0 |

Mix Phase A to room temperature. Add Phase B until homogenous

Formulation Example 13: CPW-EW1LP Cool Cream (J9-72)

| | | | | |
|---|---|---|---|---|
| A | DI Water | Distilled water | | 78.0 |
| A | Jeesperse ® CPW-EW1LP | Stearic Acid, Ceteareth-20, Cetyl Stearyl Alcohol, Sodium Polyacrylate | Jeen Int'l | 10.0 |
| A | Triethanolamine 99% | Triethanolamine | Jeen Int'l | 1.0 |
| B | Jeechem ® IPM | Isopropyl Myristate | Jeen Int'l | 2.0 |
| B | Jeesilc ® PDS-350 | Dimethicone | Jeen Int'l | 3.0 |
| B | Glycerine 99% | Glycerine | Jeen Int'l | 3.0 |
| B | Sesame Oil | *Sesamum Indicum* Seed Oil | Jeen Int'l | 2.0 |
| B | Jeecide ® G-II | Propylene Glycol, Diazolidinyl Urea, Methyl Paraben, Propyl Paraben | Jeen Int'l | 1.0 |

Mix Phase A to room temperature. Add Phase B until homogenous

| | | | | |
|---|---|---|---|---|
| A | DI Water | Distilled water | | 69.1 |
| A | Jeesperse ® CPW-EW1LP | Stearic Acid, Ceteareth-20, Cetyl Stearyl Alcohol, Sodium Polyacrylate | Jeen Int'l | 9.0 |
| A | Triethanolamine 99% | Triethanolamine | Jeen Int'l | 0.9 |
| B | Jeecide ® G-II | Propylene Glycol, Diazolidinyl Urea, Methyl Paraben, Propyl Paraben | Jeen Int'l | 1.0 |
| B | Sunscreen Blend | | Jeen Int'l | 20.0 |

Formulation Example 14: CPW-EW1LP Sunscreen (J9-74NJM)

Mix Phase A to room temperature. Add Phase B until homogenous.

Formulation Example 15: CPW-B Cool Lotion (J9-76B-NJM)

| | | | | |
|---|---|---|---|---|
| A | DI Water | Distilled water | | 76.0 |
| A | Jeesperse ® CPW-B | Beeswax, Sodium Polyacrylate | Jeen Int'l | 7.0 |
| B | Mineral Oil | Mineral Oil | Carnation | 4.0 |
| B | Jeechem ® IPM | Isopropyl Myristate | Jeen Int'l | 2.0 |
| B | Jeesilc ® PDS-350 | Dimethicone | Jeen Int'l | 3.0 |
| B | Glycerine 99% | Glycerine | Jeen Int'l | 5.0 |
| B | Sweet Almond Oil | *Prunus Amygdalus Dulcis* (Sweet Almond) Oil | Jeen Int'l | 1.0 |
| B | Avocado Oil | *Persea Gratissima* (Avocado) Oil | | 1.0 |
| B | Jeecide ® G-II | Propylene Glycol, Diazolidinyl Urea, Methyl Paraben, Propyl Paraben | Jeen Int'l | 1.0 |

Mix Phase A to room temperature. Add Phase B until homogenous.

Formulation Example 16: CPW-BC Cool Cream (J9-77 NJM)

| | | | | |
|---|---|---|---|---|
| A | DI Water | Distilled Water | | 76.0 |
| A | Jeesperse CPW-BC | *Theobroma Cacao* (Cocoa) Seed Butter, Beeswax, Yellow Refined, Sodium Polyacrylate | Jeen Int'l | 10.0 |
| B | Mineral Oil | Mineral Oil | Jeen Int'l | 4.0 |
| B | Sweet Almond Oil | *Prunus Amygdalus Dulcis* (Sweet Almond) Oil | Jeen Int'l | 1.0 |
| B | Jeesilc ® PDS-350 | Dimethicone | Jeen Int'l | 3.0 |
| B | Glycerine 99% | Glycerine | Jeen Int'l | 2.0 |
| B | Avocado Oil | *Persea Gratissima* (Avocado) Oil | Jeen Int'l | 1.0 |
| B | Jeechem ® IPM, NF | Isopropyl Myristate | Jeen Int'l | 2.0 |
| B | Jeecide ® G-II | Propylene Glycol, Diazolidinyl Urea, Methyl Paraben, Propyl Paraben | Jeen Int'l | 1.0 |

Mix Phase A at room temperature. Add Phase B until homogenous.

Formulation Example 17: CPW-BC Cool Cream (J9-78 NJM)

| | | | | |
|---|---|---|---|---|
| A | DI Water | Distilled Water | | 74.0 |
| A | Jeesperse CPW-BC | *Theobroma Cacao* (Cocoa) Seed Butter, Beeswax, Yellow Refined, Sodium Polyacrylate | Jeen Int'l | 10.0 |
| B | Mineral Oil | Mineral Oil | Jeen Int'l | 4.0 |
| B | Sweet Almond Oil | *Prunus Amygdalus Dulcis* (Sweet Almond) Oil | Jeen Int'l | 1.0 |
| B | Jeesilc ® PDS-350 | Dimethicone | Jeen Int'l | 3.0 |
| B | Glycerine 99% | Glycerine | Jeen Int'l | 2.0 |
| B | Avocado Oil | *Persea Gratissima* (Avocado) Oil | Jeen Int'l | 1.0 |
| B | Jeechem ® IPM, NF | Isopropyl Myristate | Jeen Int'l | 2.0 |
| B | BP-Biopeptide SC | *Saccharomyces*/ Selenium Ferment | Botanicals Plus | 1.0 |
| B | BP-Glucan MC | Beta Glucan | Botanicals Plus | 1.0 |
| B | Jeecide ® G-II | Propylene Glycol, Diazolidinyl Urea, Methyl Paraben, Propyl Paraben | Jeen Int'l | 1.0 |

Mix Phase A at room temperature. Add Phase B until homogenous.

Formulation Example 18: CPW-P Cool Lotion (J9-79 NJM)

| | | | | |
|---|---|---|---|---|
| A | DI Water | Distilled Water | | 82.0 |
| A | Jeesperse ® CPW-P | Cetearyl Alcohol, Sodium Polyacrylate, Stearateh-20, Polysorbate 60 | Jeen Int'l | 5.0 |
| B | Sesame Oil | *Sesamum Indicum* (Sesame) Seed Oil | Jeen Int'l | 2.0 |
| B | Jeesilc ® PDS-350 | Dimethicone | Jeen Int'l | 2.5 |
| B | Glycerine 99% | Glycerine | Jeen Int'l | 3.5 |
| B | Jeechem ® IPM, NF | Isopropyl Myristate | Jeen Int'l | 2.0 |
| B | BP-Biopeptide SC | *Saccharomyces*/ Selenium Ferment | Botanicals Plus | 1.0 |
| B | BP-Glucan MC | Beta Glucan | Botanicals Plus | 1.0 |
| B | Jeecide ® G-II | Propylene Glycol, Diazolidinyl Urea, Methyl Paraben, Propyl Paraben | Jeen Int'l | 1.0 |

Mix Phase A at room temperature. Add Phase B until homogenous.

Formulation Example 19: CPW-3 Sunscreen (J9-80B NJM)

| | | | | |
|---|---|---|---|---|
| A | DI Water | Distilled water | | 69.0 |
| A | Jeesperse ® CPW-3 | Polyethylene, Sodium Polyacrylate | Jeen Int'l | 9.0 |
| A | Jeesilc ® EM-90 | Cetyl PEG/PPG-10 Dimethicone | Jeen Int'l | 1.0 |
| B | Jeecide ® G-II | Propylene Glycol, | Jeen Int'l | 1.0 |
| B | Jeecide ® G-II | Propylene Glycol, Diazolidinyl Urea, Methyl Paraben, Propyl Paraben | Jeen Int'l | 1.0 |
| B | Sunscreen Blend | Avobenzone (9.2%), Homosalate (46.6%), Octisalate (17.5%), Octocrylene (8.6%) | Jeen Int'l | 20.0 |

Mix Phase A at room temperature. Add Phase B until homogenous.

Formulation Example 20: CPW5-PVPK-30 Lifting Skin Renewal (J9-84B)

| | | | | |
|---|---|---|---|---|
| A | DI Water | Distilled water | | 88.0 |
| A | Jeesperse ® CPW5-PVPK-30 | Polyethylene, Polyvinylpyrrolidone, Sodium Polyacrylate | Jeen Int'l | 10.0 |

| | | | | |
|---|---|---|---|---|
| B | Jeecide ® G-II | Propylene Glycol, Diazolidinyl Urea, Methyl Paraben, Propyl Paraben | Jeen Int'l | 1.0 |
| B | Jeesilc ® PDS-1 | Dimethicone | Jeen Int'l | 1.0 |

Mix Phase A. Mix Phase B until homogenous. Add Phase B to Phase A mix until homogenous.

Formulation Example 21: CPW-BC Natural Hydrogel Cream (J9-90 NJM)

| | | | | |
|---|---|---|---|---|
| A | DI Water | Distilled water | | 76.0 |
| A | Jeesperse ® CPW-BC | *Theobroma Cacao* (Cocoa) Seed Butter, Beeswax, Yellow Refined, Sodium Polyacrylate | Jeen Int'l | 10.0 |
| A | Coconut Oil | *Cocos Nucifera* Oil | Jeen Int'l | 3.0 |
| A | Shea Butter | *Butyrospermum Parkii* Butter | Jeen Int'l | 5.0 |
| B | Jeechem ® CTG | Caprylic/Capric Triglyceride | Jeen Int'l | 5.0 |
| B | Jeecide ® CAP-5 | Phenoxyethanol, Caprylyl Glycol, Potassium Sorbate, Water, Hexylene Glycol | Jeen Int'l | 1.0 |

Mix Phase A at room temperature. Add Phase B until homogenous.

Formulation Example 22: CPW-EW1LP 110 Lotion (J10-11D)

| | | | | |
|---|---|---|---|---|
| A | DI Water | Distilled water | | 78.0 |
| A | Triethanolamine 99% | Triethanolamine | Jeen Int'l | 1.0 |
| A | Jeesperse ® CPW-EW1LP | Stearic Acid, Ceteareth-20, Cetyl Stearyl Alcohol, Sodium Polyacrylate | Jeen Int'l | 10.0 |
| B | Jeechem ® IPM | Isopropyl Myristate | Jeen Int'l | 2.0 |
| B | Glycerine 99% | Glycerine | Jeen Int'l | 3.0 |
| B | Sesame Oil | *Sesamum Indicum* Seed Oil | Jeen Int'l | 2.0 |
| B | Jeesilc ® 110 | Dimethicone | Jeen Int'l | 2.0 |
| B | Baby Powder Scent | Fragrance | | 1.0 |
| B | Jeecide ® G-II | Propylene Glycol, Diazolidinyl Urea, Methyl Paraben, Propyl Paraben | Jeen Int'l | 1.0 |

Mix Phase A. Add Phase B until homogenous. Add Phase C and mix.

Formulation Example 23: CPW-2 110 Lotion (J10-12B)

| | | | | |
|---|---|---|---|---|
| A | DI Water | Distilled water | | 80.0 |
| A | Jeesperse ® CPW-2 | Polyethylene, Sodium Polyacrylate | Jeen Int'l | 10.0 |
| B | Jeechem ® IPM | Isopropyl Myristate | Jeen Int'l | 2.0 |
| B | Glycerine 99% | Glycerine | Jeen Int'l | 3.0 |
| B | Sesame Oil | *Sesamum Indicum* Seed Oil | Jeen Int'l | 2.0 |
| B | Jeesilc ® 110 | Dimethicone | Jeen Int'l | 2.0 |
| B | Jeecide ® G-II | Propylene Glycol, Diazolidinyl Urea, Methyl Paraben, Propyl Paraben | Jeen Int'l | 1.0 |

Mix Phase A to room temperature. Add Phase B until homogenous.

Formulation Example 24: LV-CPW Spray Lotion (J10-45 JM)

| | | | | |
|---|---|---|---|---|
| A | Deionized Water | Water | | 90.0 |
| A | Jeesperse CPW-CG-T | Cetyl Alcohol, Sodium Acrylate/Sodium Acryloyl Dimethyl Taurate Copolymer, Glyceryl Stearate | Jeen Int'l | 1.5 |
| A | Jeechem ® ISP | Isostearyl Palmitate & Triisostearyl Citrate | Jeen Int'l | 2.0 |
| A | Jeesperse CPW-S | *Helianthus Annuus* (Sunflower) Seed Wax, | Jeen Int'l | 0.5 |
| A | Jeesperse CPW-S | *Helianthus Annuus* (Sunflower) Seed Wax, 2-Propenoic Acid, Homopolymer | Jeen Int'l | 0.5 |
| B | Jeesilc ® DMC-153 | Dimethicone, Dimethiconol | Jeen Int'l | 3.0 |
| B | Jeesorb L-20 | Polysorbate 20 | Jeen Int'l | 1.9 |
| B | Jeecide ® GII | Propylene Glycol, | Jeen Int'l | 0.8 |

Mix Phase A at room temperature. Add Phase B until homogenous.

Formulation Example 25: HV-CPW Spray Lotion (J10-45A JM)

| | | | | |
|---|---|---|---|---|
| A | Deionized Water | Water | | 90.0 |
| A | Jeesperse CPW-CG-T | Cetyl Alcohol, Sodium Acrylate/Sodium Acryloyl Dimethyl Taurate Copolymer, Glyceryl Stearate | Jeen Int'l | 2.0 |
| A | Jeechem ® ISP | Isostearyl Palmitate & Triisostearyl Citrate | Jeen Int'l | 2.0 |
| A | Jeesperse CPW-S | *Helianthus Annuus* (Sunflower) Seed Wax, 2-Propenoic Acid, Homopolymer | Jeen Int'l | 0.5 |
| B | Jeesilc ® DMC-153 | Dimethicone, Dimethiconol | Jeen Int'l | 3.0 |
| B | Jeesorb ® STS-20 | Polysorbate 65 | Jeen Int'l | 1.7 |
| B | Jeecide ® GII | Propylene Glycol, Diazolidinyl Urea, Methyl Paraben, Propyl Paraben | Jeen Int'l | 0.8 |

Mix Phase A at room temperature. Add Phase B until homogenous.

Formulation Example 26: LV-CPW Spray Lotion (J10-45B JM)

| | | | | |
|---|---|---|---|---|
| A | Deionized Water | Water | | 90.0 |
| A | Jeesperse ® CPW-CG-T | Cetyl Alcohol, Sodium Acrylate/Sodium Acryloyl Dimethyl Taurate Copolymer, Glyceryl Stearate | Jeen Int'l | 1.5 |
| A | Jeechem ® ISP | Isostearyl Palmitate & Triisostearyl Citrate | Jeen Int'l | 2.0 |
| A | Jeesperse CPW-S | *Helianthus Annuus* (Sunflower) Seed Wax, 2-Propenoic Acid, Homopolymer | Jeen Int'l | 0.4 |
| B | Jeesilc ® DMC-153 | Dimethicone, Dimethiconol | Jeen Int'l | 3.0 |
| B | Jeesorb ® STS-20 | Polysorbate 65 | Jeen Int'l | 2.0 |
| B | Jeecide ® GII | Propylene Glycol, Diazolidinyl Urea, Methyl Paraben, Propyl Paraben | Jeen Int'l | 0.8 |

Mix Phase A at room temperature. Add Phase B until homogenous.

Formulation Example 27: CPW-5 Cream (J11-2 NJM)

| | | | | |
|---|---|---|---|---|
| A | DI Water | Distilled Water | | 80.5 |
| A | Jeesperse ® CPW-5 | Polyethylene, Sodium Polyacrylate | Jeen Int'l | 5.0 |
| B | Coconut Oil | *Cocos Nucifera* (Coconut) Oil | Jeen Int'l | 3.0 |
| B | Avocado Oil | *Persea Gratissima* (Avocado) Oil | Jeen Int'l | 3.0 |
| B | Jeesilc ® PDS-350 | Dimethicone | Jeen Int'l | 2.0 |
| B | Glycerine 99% | Glycerine | Jeen Int'l | 3.5 |
| B | Jeechem ® IPM, NF | Isopropyl Myristate | Jeen Int'l | 2.0 |
| B | Jeecide ® G-II | Propylene Glycol, Diazolidinyl Urea, Methyl Paraben, Propyl Paraben | Jeen Int'l | 1.0 |

Mix Phase A at room temperature. Add Phase B until homogenous.

| | | | | |
|---|---|---|---|---|
| A | DI Water | Distilled water | | 68.0 |
| A | Jeesperse ® CPW-BC | *Theobroma Cacao* (Cocoa) Seed Butter, Yellow Beeswax, Sodium Polyacyrlate | Jeen Int'l | 6.50 |
| A | PVPK-30 | Polvinylpyrrolidone | ISP | 3.50 |
| A | BTD 11S2 | Titanium Dioxide (AND) Triethoxycaprylylsilane | Kobo | 4.00 |
| B | Jeecide ® G-II | Propylene Glycol, Diazolidinyl Urea, Methyl Paraben, Propyl | Jeen Int'l | 0.50 |
| B | Jeecide ® G-II | Propylene Glycol, Diazolidinyl Urea, Methyl Paraben, Propyl Paraben | Jeen Int'l | 0.50 |
| B | Jeesilc ® PDS-1 | Dimethicone | Jeen Int'l | 4.00 |
| B | Mica | Mica | Kobo | 4.00 |
| B | Interfine Green | Mica and Titanium Dioxide | Kobo | 7.50 |

Formulation Example 28: CPW-BC Eye Shadow (J11-37)

Mix Phase A at room temperature. Add Phase B and homogenize.

Formulation Example 29: CPW-S Sunscreen (J11-53 NJM)

| | | | | |
|---|---|---|---|---|
| A | DI Water | Distilled Water | | 68.0 |
| A | Jeesperse ® CPW-S | Sunflower Wax, Sodium Polyacrylate | Jeen Int'l | 10.0 |
| A | Jeesilc ® EM-90 | Cetyl Peg/Ppg-10 Dimethicone | Jeen Int'l | 1.0 |
| B | Jeecide ® G-II | Propylene Glycol, Diazolidinyl Urea, Methyl Paraben, Propyl Paraben | Jeen Int'l | 1.0 |
| B | Sunscreen Blend | | Jeen Int'l | 20.0 |

Mix Phase A to room temperature. Add Phase B until homogenous.

Formulation Example 30: CPW-BC Eye Shadow (J11-83 NJM)

| | | | | |
|---|---|---|---|---|
| A | DI Water | Distilled Water | | 66.5 |
| A | Jeesperse CPW-BC | *Theobroma Cacao* (Cocoa) Seed Butter, Beeswax, Yellow Refined, Sodium Polyacrylate | Jeen Int'l | 3.0 |
| A | Jeesilc ® DMBF Aqua Base | Dimethicone (and) Cetyl PEG/PPG-10 Dimethicone (and) Bis-Vinyl Dimethicone/Dimethicone Copolymer | Jeen Int'l | 7.0 |
| A | Jeesilc ® PDS.1 | Dimethicone | Jeen Int'l | 4.0 |
| A | Mineral Oil | Mineral Oil | Jeen Int'l | 0.5 |
| A | PVPK-30 | Polyvinylpyrrolidone | ISP | 4.0 |
| A | BTD 11S2 | Titanium Dioxide (and) Triethoxycaprylylsilane | Kobo | 2.0 |
| A | Jeecide ® GII | Propylene Glycol, Diazolidinyl Urea, Methyl Paraben, Propyl Paraben | Jeen Int'l | 1.0 |
| B | KobomicaL-25 | Mica | Kobo | 3.0 |
| B | KTZ Shimmer Green | Mica And Titanium Dioxide | Kobo | 5.0 |
| B | Bichroma Magenta | Bismuth Oxychloride And Mica And Carmine | Impact Color | 2.0 |
| B | Diamond Red Rose | Mica And Titanium Dioxide And Carmine And Tin Oxide And Methicone | Impact Color | 1.0 |
| B | Jeesilc ® DMC 19-3 | Peg-12 Dimethicone | Jeen Int'l | 1.0 |

Mix Phase A until homogenous. Add in Phase B and mix.

Formulation Example 31: CPW-CG-T Creamy Sunscreen (J11-84 NJM)

| | | | | |
|---|---|---|---|---|
| A | DI Water | Distilled Water | | 56.0 |
| A | Jeesperse CPW-CGT | Cetyl Alcohol, Sodium Acrylate/Sodium Acryloyl Dimethyl Taurate Copolymer, Glyceryl Stearate | Jeen Int'l | 4.0 |
| A | Jeesilc® DMBF | Dimethicone, Bis-Vinyl Dimethicone/Dimethicone Copolymer | Jeen Int'l | 9.0 |
| B | Jeesperse T50TN | $C_{12-15}$ Alkyl Benzoate, Titanium Dioxide, Triethoxycaprylylsilane, Castor Oil Phosphate | Jeen Int'l | 17.0 |
| B | Jeeesperse ZO-65OP | Zinc Oxide USP (and)Dimethicone(and) Octyl Palmitate | Jeen Int'l | 7.0 |
| B | Jeesilc® 3D-5 | Dimethicone Crosspolymer-3, Cyclomethicone | Jeen Int'l | 2.0 |
| B | Jeesilc® DMC-153 | Dimethicone, Dimethiconol | Jeen Int'l | 4.0 |
| B | Jeecide® G-II | Propylene Glycol, Diazolidinyl Urea, Methyl Paraben, Propyl Paraben | Jeen Int'l | 1.0 |

Add all ingredients from Phase A and mix until uniform. Add Phase B ingredients, one at the time and mix well until homogenous

Formulation Example 32: CPW-Sun21 Anti-Bacterial (J11-88B NJM)

| | | | | |
|---|---|---|---|---|
| A | DI Water | Distilled water | | 30 |
| A | SDA 40 | Ethanol | | 63 |
| A | AMPD | Amino Methyl Propanediol | Angus | 0.5 |
| B | Glycerin 99.7% USP | Glycerin | Jeen Int'l | 3.0 |
| B | Jeesperse CPW-SUN21 | *Helianthux Annuus* (Sunflower) Seed Wax and Acrylates/$C_{10-30}$ Alkyl Crosspolymer | Jeen Int'l | 3.5 |

Mix Phase A to room temperature. Add Phase B until homogenous.

Formulation Example 33: CPW-S Natural Hydrogel (11-38NJM)

| | | | | |
|---|---|---|---|---|
| A | DI Water | Water | | 76.0 |
| A | Jeesperse® CPW-S | Sunflower Wax, Sodium Polyacrylate | Jeen Int'l | 6.00 |
| A | Shea Butter | Shea (*Butyrospermum Parkii*) Butter | Jeen Int'l | 5.00 |
| A | Safflower Oil | *Carthamus Tinctorius* (Safflower) Seed Oil | Jeen Int'l | 2.00 |
| A | Coconut Oil | *Cocos Nucifera* (Coconut) OIL | Jeen Intl | 5.00 |
| A | Jeechem® CTG | Caprylic/Capric Triglyceride | Jeen Int'l | 5.00 |
| B | Jeecide® CAP-5 | Phenoxyethanol, Caprylyl Glycol, Potassium Sorbate, Water, Hexylene Glycol | Jeen Int'l | 1.00 |

Mix Phase A at room temperature. Add Phase B and mix until homogenous.

Formulation Example 34: CPW-CG-T Moisture Lotion (J11-92 NJM)

| | | | | |
|---|---|---|---|---|
| A | Deionized Water | Water | | 83.0 |
| A | Jeesperse® CPW-CGT | Cetyl Alcohol, Sodium Acrylate/Sodium Acryloyl Dimethyl Taurate Copolymer, Glyceryl Stearate, Caprylic/Capric Triglyceride | Jeen Int'l | 5.0 |
| A | Glycerin | Glycerin | Jeen Int'l | 5.0 |
| A | Jeesilc® PDS 350 | Dimethicone | Jeen Int'l | 2.0 |
| B | Jeesilc® 110 | Dimethicone | Jeen Int'l | 4.5 |
| B | Jeecide® GII | Propylene Glycol, Diazolidinyl Urea, Methyl Paraben, Propyl Paraben | Jeen Int'l | 0.5 |

Mix Phase A at room temperature. Add Phase B until homogenous

Formulation Example 35: CPW-CG-T Eye Shadow (J11-95 NJM)

| | | | | |
|---|---|---|---|---|
| A | DI Water | Distilled Water | | 68.5 |
| A | Jeesperse® CPW-CG-T | Cetyl Alcohol, Sodium Acrylate/Sodium Acryloyl Dimethyl Taurate Copolymer, Glyceryl Stearate, Caprylic/Capric Triglyceride | Jeen Int'l | 3.0 |
| A | Jeesilc® DMBF Aqua Base | Dimethicone (and) Cetyl PEG/PPG-10 Dimethicone (and) Bis-Vinyl Dimethicone/Dimethicone Copolymer | Jeen Int'l | 6.0 |
| A | Jeesilc® PDS1 | Dimethicone | Jeen Int'l | 4.0 |
| A | Mineral Oil | Mineral Oil | Jeen Int'l | 0.5 |
| A | PVPK-30 | Polyvinylpyrrolidone | ISP | 4.0 |
| A | BTD 11S2 | Titanium Dioxide (AND) Triethoxycaprylsilane | Kobo | 2.0 |
| A | Jeecide® GII | Propylene Glycol, Diazolidinyl Urea, Methyl Paraben, Propyl Paraben | Jeen Int'l | 1.0 |
| B | Kobomica L-25 | MICA | Kobo | 3.0 |
| B | KTZ Bronze | Mica and Titanium Dioxide | Kobo | 5.0 |
| B | Chromatique Cupreous Brown | Mica and Iron Oxide | Impact Color | 2.0 |
| B | El Dorado Wine Red | Mica and Iron Oxide | Impact Color | 1.0 |

Mix Phase A at room temperature. Add Phase B until homogenous.

Formulation Example 36: CPW-BC Lip Paint (J12-25)

| | | | | |
|---|---|---|---|---|
| A | Water | Water | | 61.2 |
| A | Jeesperse CPW-BC | *Theobroma Cacao* (Cocoa) Seed Butter, Beeswax, Yellow Refined, Sodium Polyacrylate | Jeen Int'l | 5.0 |

-continued

| | | | | |
|---|---|---|---|---|
| A | Shea Butter | Shea (*Butyrospermum Parkii*) Butter | Jeen Int'l | 5.0 |
| A | Coconut Oil | *Cocos Nucifera* (Coconut) Oil | Jeen Int'l | 4.0 |
| A | Jeechem ® CTG | Caprylic/Capric | Jeen Int'l | 4.0 |
| A | Jeechem ® CTG | Caprylic/Capric Triglyceride | Jeen Int'l | 4.0 |
| A | Sesame Oil | *Sesamum Indicum* (Sesame) Seed Oil | Jeen Int'l | 2.0 |
| A | Jeecide ® GII | Propylene Glycol, Diazolidinyl Urea, Methyl Paraben, Propyl Paraben | Jeen Int'l | 1.0 |
| A | *Stevia* | *Eupatorium Rebaudianum Bertoni* Leaf Extract | Fabrichem Inc | 0.1 |
| A | Vanilla Lace Scent | Fragance | Fragance Resources | 0.1 |
| A | Jeesilc ® EM-90 | Cetyl Peg/Ppg-10 Dimethicone | Jeen Int'l | 2.0 |
| B | Performa V 825 | Synthetic Wax | New Phase | 2.5 |
| B | SW40R7C | Synthetic Wax/Red 7 | Kobo | 6.5 |
| B | SW60ER | Synthetic Wax/Red Oxide | Kobo | 0.8 |
| B | SW55EB | Synthetic Wax/Black Oxide | Kobo | 0.2 |
| B | Mica | Mica | Kobo | 2.6 |

Mix Phase A at Room temperature. Add Phase B mix until homogenous.

Formulation Example 37: CPW-BC Lip Paint (J12-25B)

| | | | | |
|---|---|---|---|---|
| A | Water | Water | | 56.2 |
| A | Jeesperse CPW-BC | *Theobroma Cacao* (Cocoa) Seed Butter, | Jeen Int'l | 10.0 |
| A | Jeesperse CPW-BC | *Theobroma Cacao* (Cocoa) Seed Butter, Beeswax, Yellow Refined, Sodium Polyacrylate | Jeen Int'l | 10.0 |
| A | Shea Butter | Shea (*Butyrospermum Parkii*) Butter | Jeen Int' | 5.0 |
| A | Coconut Oil | *Cocos Nucifera* (Coconut) Oil | Jeen Intl | 4.0 |
| A | Jeechem ® CTG | Caprylic/Capric Triglyceride | Jeen Int'l | 4.0 |
| A | Sesame Oil | *Sesamum Indicum* (Sesame) Seed Oil | Jeen Int'l | 2.0 |
| A | Jeecide ® GII | Propylene Glycol, Diazolidinyl Urea, Methyl Paraben, Propyl Paraben | Jeen Int'l | 1.0 |
| A | *Stevia* | *Eupatorium Rebaudianum Bertoni* Leaf Extract | Fabrichem Inc | 0.1 |
| A | Vanilla Lace Scent | Fragance | Fragance Resources | 0.1 |
| A | Jeesilc ® EM-90 | Cetyl PEG/PPG-10 Dimethicone | Jeen Int'l | 2.0 |
| B | Performa V 825 | Synthetic Wax | New Phase | 2.5 |
| B | SW40R7C | Synthetic Wax/Red 7 | Kobo | 6.5 |
| B | SW60ER | Synthetic Wax/Red Oxide | Kobo | 0.8 |
| B | SW55EB | Synthetic Wax/Black Oxide | Kobo | 0.2 |

Mix Phase A at Room temperature. Add Phase B mix until homogenous.

Formulation Example 38: CPW-2-Crosspolymer Cream (J12-27 NJM)

| | | | | |
|---|---|---|---|---|
| A | DI Water | Distilled Water | | 87.0 |
| A | Jeesperse ® CPW-2-Crosspolymer | Polyethylene, Sodium Polyacrylate, Dimethicone/Vinyl Dimethicone Crosspolymer | Jeen Int'l | 10.0 |
| B | Jeesilc ® PDS-350 | Dimethicone (Polydimethylsiloxane) | Jeen Int'l | 2.0 |
| B | Jeecide ® G-II | Propylene Glycol, Diazolidinyl Urea, Methyl Paraben, Propyl Paraben | Jeen Int'l | 1.0 |

Mix Phase A to room temperature. Add Phase B until homogenous.

Formulation Example 39: CPW-2-Crosspolymer Cream (J12-27ANJM)

| | | | | |
|---|---|---|---|---|
| A | DI Water | Distilled Water | | 87.0 |
| A | Jeesperse ® CPW-2-Crosspolymer | Polyethylene, Sodium Polyacrylate, Dimethicone/Vinyl Dimethicone Crosspolymer | Jeen Int'l | 10.0 |
| B | Jeesilc ® DMC-153 | Dimethicone, Dimethiconol | Jeen Int'l | 2.0 |
| B | Jeecide ® G-II | Propylene Glycol, Diazolidinyl Urea, Methyl Paraben, Propyl Paraben | Jeen Int'l | 1.0 |

Mix Phase A to room temperature. Add Phase B until homogenous.

Formulation Example 40: CPW-2-Crosspolymer Cream (J12-27B NJM)

| | | | | |
|---|---|---|---|---|
| A | DI Water | Distilled water | | 87.0 |
| A | Jeesperse ® CPW-2-Crosspolymer | Polyethylene, Sodium Polyacrylate, Dimethicone/Vinyl Dimethicone Crosspolymer | Jeen Int'l | 10.0 |
| B | Jeesilc ® DMBF | Dimethicone, Bis-Vinyl Dimethicone/Dimethicone Copolymer, | Jeen Int'l | 2.0 |
| B | Jeecide ® G-II | Propylene Glycol, Diazolidinyl Urea, Methyl Paraben, Propyl Paraben | Jeen Int'l | 1.0 |

Mix Phase A to room temperature. Add Phase B until homogenous.

Formulation Example 41: CPW-2-Crosspolymer Cream (J12-27C NJM)

| | | | | |
|---|---|---|---|---|
| A | DI Water | Distilled water | | 87.0 |
| A | Jeesperse ® CPW-2-Crosspolymer | Polyethylene, Sodium Polyacrylate, Dimethicone/Vinyl Dimethicone Crosspolymer | Jeen Int'l | 10.0 |

-continued

| | | | | |
|---|---|---|---|---|
| B | Jeesilc ® PDS 1.0 | Dimethicone | Jeen Int'l | 2.0 |
| B | Jeecide ® G-II | Propylene Glycol, Diazolidinyl Urea, Methyl Paraben, Propyl Paraben | Jeen Int'l | 1.0 |

Mix Phase A to room temperature. Add Phase B until homogenous.

Formulation Example 42: CPW-S Mascara (J8-87 and J8-88)

| | | | | | |
|---|---|---|---|---|---|
| A | Water, Sunflower Wax (and) Sodium Polyacrylate (Jeesperse ® CPW-S) Hexylene Glycol, Caprylyl Glycol, Iodopropynyl Butylcarbamate, Phenoxyethanol. (Jeecide ® CAP-5) | Jeen Int'l | 20 | 40 | |
| B | Water, Polyurethane, Ethanol | | 30.7 | — | |
| B | Isododecane, Silicone Acrylate | | — | 17.4 | |
| C | Cetyl PEG/PPG-10 Dimethicone | Jeen Int'l | — | 100 | Add water or other aqueous medium to |
| C | Iron Oxide (77499), Triethoxycaprylyl Silane | | 9.00 | 10.5 | Phase A and mix. Add in Phase B and mix. Add in Phase C and mix. |

Formulation Example 41: Antioxidant Emulsion (Cream) from CPFA Concentrate Incorporating All Ingredients (Jeesperse CPW-2/JAW/AOX,C)

| | | |
|---|---|---|
| A | CPFA Concentrate (INCI: Water, Polyethylene, Dimethicone, Iosopropyl Isostearate, Sodium Polyacrylate, Magnesium Ascorbyl Phosphate, Phenoxyethanol | 40% |
| B | Water | 60% |

Add Phase A to a mixing vessel. Start mixing. Add Phase B to Phase A while mixing. Water temperature can be less than the melt point of the CPW-2/JAW/AOX,C. Mix until uniform.

Formulation Example 42: Antioxidant Emulsion (Cream) with CPFA Concentrate (Jeesperse CPW-2/JAW,U)

| | | |
|---|---|---|
| A | CPFA Concentrate - Water, Polyethylene, Sodium Polyacrylate, Phenoxyethanol | 30% |
| A | Dimethicone | 3% |
| A | Isopropyl Isostearate | 2% |
| A | Magnesium Ascorbyl Phosphate | 1% |
| B | Water | 64% |

Add Phase A to a mixing vessel. Start mixing. Add Phase B to Phase A while mixing. Water temperature can be less than the melt point of the Jeesperse CPW-2/JAW,U. Mix until uniform.

Formulation Example 43: Body Cream from CPFA Concentrate Containing All Ingredients (Including Neutralizer) (Jeesperse CPW-EW-1LP/JAW,N)

| | | |
|---|---|---|
| A | CPFA Concentrate - Water, Stearic Acid, Ceteareth-20, Cetearyl Alcohol, Dimethicone, Carbomer, TEA, Phenoxyethanol (Commercially available Jeesperse CPW-EW-1LP/JAW, N-C | 30% |
| B | Water | 70% |

Add Phase A to a mixing vessel. Start mixing. Add Phase B to Phase A while mixing. Water temperature can be less than the melt point of Jeesperse CPW-EW-1LP/JAW,N. Mix until uniform.

Formulation Example 44: Body Cream form CPFA Concentrate (Including Neutralizer) (Jeesperse CPW-EW-1LP/JAW,N-U)

| | | |
|---|---|---|
| A | Water, Stearic Acid, Ceteareth-20, Cetearyl Alcohol, Carbomer, TEA, Phenoxyethanol (Jeesperse CPW-EW-1LP/JAW, N-U) | 27% |
| A | Dimethicone | 3% |
| B | Water | 70% |

Add Phase A to a mixing vessel. Start mixing. Add Phase B to Phase A while mixing. Water temperature can be less than the melt point of the Jeesperse CPW-EW-1LP/JAW,N Mix until uniform.

Formulation Example 44: Body Cream form CPFA Concentrate (No Neutralizer) (Jeesperse CPW-EW-1LP/JAW,U)

| | | |
|---|---|---|
| A | Water, Stearic Acid, Ceteareth-20, Cetearyl Alcohol, Carbomer, Phenoxyethanol (Jeesperse CPW-EW-1LP/JAW, U) | 27% |
| B | Dimethicone | 3% |
| C | Water | 69% |
| D | Triethanolamine | 1% |

Add Phase A to a mixing vessel. Start mixing. Add Phase B to Phase A while mixing. Water temperature can be less than the melt point of the Jeesperse CPW-EW-1LP/JAW,U. Add Phase C while mixing. Add Phase D to increase viscosity. Mix until uniform.

Formulation Example 45: CPFA Anionic

| | |
|---|---|
| Water | 89% |
| Isopropyl Isostearate | 5% |
| CPFA (50% Polyacrylate; 30%, Isopropyl Isostearate; 20% Polyglyceryl-3 Stearate) | 1.0% |
| Caprylic Capric/Triglyceride | 4% |
| Phenoxyethanol | 1% |

Formulation Example 45: CPFA Cationic

| | |
|---|---|
| Water | 70% |
| Isopropyl Isostearate | 5% |
| Dimethicone | 10% |
| CPFA (40% Polquarternium 37; 50% Isopropyl Isostearate; 10% Polyglyceryl-3 Stearate) | |
| Caprylic Capric/Triglyceride | 4% |
| Glycerine | 2% |
| Phenoxyethanol | 1% |

Formulation Example 46: CPFA Gum

| | |
|---|---|
| Water | 70% |
| Isopropyl Isostearate | 5% |
| Dimethicone | 6% |
| CPFA (30% Sodium Alginate; 60% Isopropyl Isostearate; 5% Sorbitan Stearate; 5% Polyglyceryl-3 Stearate) | |
| Caprylic Capric/Triglyceride | 4% |
| Glycerine | 6% |
| Phenoxyethanol | 1% |

Formulation Example 47: Emulsion/Hydrogel Formed without Mixing or Heating

Certain CPFAs can be used to form a hydrogel/emulsion without mixing. For example, a CPFA can be combined with an ester and a silicone to coat a powder (mica in the present example). In this Example 47, all of the Phase A ingredients are combined—for example, with a ribbon blender. A water phase (Phase B) can be added on top of this paste. Thereafter, iron oxide and other pigments (e.g., $TiO_2$ and ZnO) can be added to the paste, to create a color cosmetic product. Alternatively, the paste can be pressed into a container and applied with a wet applicator (e.g., brush), or extruded into a pencil.

| Phase | Ingredient | % wt/wt |
|---|---|---|
| A | Mica | 10% |
| A | Isopropyl Myristate | 10% |
| A | Dimethicone | 9% |
| A | Phenoxyethanol | 1% |
| A | CPFA (30% Sodium Acrylate/Sodium Acryloyl Dimethyl Taurate Copolymer; 25% Glycol Stearate; 25% Cetyl Alcohol; 10% Caprylic/Capric Triglyceride; 10% Glyceryl Stearate)* | |
| A | Butylene Glycol | 20% |
| B | Water | 40% |

*Available from Jeen International under the tradename Jeesperse ® ICE-T-LB-T-NS.

Formulation Examples 48 and 49 (Hand Sanitizer)

Examples 48 and 49 illustrate two topical, hydroalcoholic formulations that can be used as an antimicrobial hand sanitizer. Both formulations use a CPFA of the present invention containing 35% Cetearyl Alcohol, 35% PEG-150 Distearate, and 30% Polyquaternium 37. Both of these formulations are made by mixing Phase A ingredients, and then adding Phase B ingredients, mixing until homogenous. No heating is required.

Formulation Example 48

| Phase | Ingredient | % wt/wt |
|---|---|---|
| A | Water | 41 |
| A | Ethanol | 40 |
| A | Glycerin | 9 |
| B | CPFA (35% Cetearyl Alcohol; 35% PEG-150 Distearate; and 30% Polyquaternium 37) | 9 |
| B | Phenoxyethanol | 1 |

Formulation Example 49

| Phase | Ingredient | % wt/wt |
|---|---|---|
| A | Water | 41 |
| A | Ethanol | 40 |
| A | Glycerin | 9 |
| B | CPFA (35% Cetearyl Alcohol; 35% PEG-150 Distearate; and 30% Polyquaternium 37) | 5 |
| B | Phenoxyethanol | 1 |
| B | Fragrance/perfume | 4 |

While particular embodiments of the present invention have been illustrated and described, those skilled in the art can readily make changes and modifications to these embodiments without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

We claim:

1. An anhydrous cold process formulation aid in the form of a flake, slab, powder, a paste, a semi-solid, or a slurry consisting essentially of
    (i) a polymer having an aliphatic backbone selected from a polyquaternium polymer and a polymer having a plurality of pendant groups selected from alkali metal carboxylate groups and ammonium carboxylate groups, and
    (ii) a wax selected from the group consisting of natural waxes and synthetic waxes, wherein if the wax is not micronized and is not self-emulsifying, the ratio, by weight, of the non-micronized wax to the polymer having an aliphatic backbone is from about 60:40 to 80:20, and if the wax is a micronized wax or a self-emulsifying wax, the ratio, by weight, of wax to polymer backbone is 70:30 to 98:2,
    wherein when the anhydrous cold process formulation aid is mixed with an aqueous medium at a temperature not exceeding the melt point of the wax or the melt point of the cold process formulation aid, a hydrogel or an emulsion is formed.

2. The anhydrous cold process formulation aid of claim 1 wherein the polymer having an aliphatic backbone has pendant groups that are alkali metal or ammonium carboxylate groups.

3. The anhydrous cold process formulation aid of claim 1 wherein the polymer having an aliphatic backbone is the sodium salt of poly(acrylic acid).

4. The anhydrous cold process formulation aid of claim 1 wherein the polymer having an aliphatic backbone is a polyquaternium.

5. The anhydrous cold process formulation aid of claim 4 wherein the polymer is a polyquaternium selected from the group consisting of Polyquaternium 7 and Polyquaternium 37.

6. The anhydrous cold process formulation aid of claim 1 wherein the wax is a natural wax selected from the group consisting of sunflower wax, candelilla wax, olive wax, and carnauba wax.

7. The anhydrous cold process formulation aid of claim 1 wherein the wax is a synthetic wax selected from the group consisting of polyethylene, glyceryl monostearate, paraffin, and polyglyceryl-3 stearate.

8. The anhydrous cold process formulation aid of claim 1 wherein the wax is a micronized wax, having a mean particle size from 5 to 50 microns.

9. The anhydrous cold process formulation aid of claim 1 wherein when mixed with an aqueous medium at a temperature not exceeding 30° C., the cold process formulation aid forms a hydrogel or an emulsion.

10. The anhydrous cold process formulation aid of claim 1 further containing a polymer having a polysaccharide backbone.

11. A method for producing a eutectic, cold-process formulation aid comprising the sequential steps of:
(i) adding a wax to a vessel, heating the wax to a temperature that is at least about 5° C. above the melt point of the wax, mixing the wax until a homogenous batch of molten wax is achieved;
    (a) adding a polymer having an aliphatic backbone selected from a polyquaternium polymer and a polymer having a plurality of pendant groups selected from alkali metal carboxylate groups and ammonium carboxylate groups to the batch of molten wax from step (i), mixing the wax and the polymer together, while heating to a temperature of at least about 5° C. above the higher of the melt point of the wax or (b) the softening point of the polymer, until a homogenous mixture is produced;
(ii) cooling the mixture from step (i) to a temperature of about 5° C. above the congealing point of the mixture;
(iii) pouring the mixture from step (ii) onto a chilled surface having a temperature from about −10° C. to about 10° C., producing a cold-process formulation aid in the form of a solid wax, or wax-like substance;
wherein if the wax is not micronized and is not emulsifying, the ratio, by weight, of the non-micronized/non-emulsifying wax to the polymer having an aliphatic backbone is from about 60:40 to 80:20, and if the wax is a micronized wax or an emulsifying wax, the ratio, by weight, of wax to polymer backbone is 70:30 to 98:2; and
wherein when mixed with an aqueous medium, the cold-process formulation aid forms a hydrogel or an emulsion.

12. The method for producing a cold-process formulation aid according to claim 11 wherein
    (a) in step (i), two waxes, a first wax and a second wax, are combined and the two waxes are heated to a temperature that is at least about 5° C. above the higher of (x) the melt point of the first wax and (y) the melt point of the second wax, and
    (b) in step (ii), after addition of a polymer having an aliphatic backbone selected from a polyquaternium polymer or a polymer having an aliphatic backbone with a plurality of pendant groups selected from alkali metal carboxylate groups and ammonium carboxylate groups, the two waxes and the polymer are mixed together, while heating to a temperature of at least about 5° C. above the higher of (x) the melt point of the first wax, (y) the melt point of the second wax, or (z) the softening point of the polymer.

13. The method for producing a cold-process formulation aid according to claim 11 wherein in step (ii), two polymers having an aliphatic backbone selected from a polyquaternium polymer and a polymer having a plurality of pendant groups selected from alkali metal carboxylate groups and ammonium carboxylate groups, a first polymer and a second polymer, are mixed with the wax, while heating to a temperature of at least about 5° C. above the higher of (xx) the melt point of the wax, (yy) the softening point of the first polymer, or (zz) the softening point of the second polymer.

14. The method for producing a cold-process formulation aid according to claim 12 wherein in step (ii), two polymers having an aliphatic backbone selected from a polyquaternium polymer and a polymer having a plurality of pendant groups selected from alkali metal carboxylate groups and ammonium carboxylate groups, a first polymer and a second polymer, are mixed with the two waxes, while heating to a temperature of at least about 5° C. above the higher of (aa) the melt point of the first wax, (bb) the melt point of the second wax, (cc) the softening point of the first ionic polymer, or (dd) the softening point of the second ionic polymer.

15. An anhydrous cold process formulation aid that is directly soluble in a cosmetically-acceptable ester or a Caprylic/Capric Triglyceride without a petroleum-derived solvent, the cold process formulation aid consisting essentially of
    (a) a polymer having an aliphatic backbone selected from a polyquaternium polymer and a polymer having a plurality of pendant groups selected from alkali metal carboxylate groups and ammonium carboxylate groups; and
    (b) a self-emulsifying wax, and
    wherein the ratio of (a) the polymer having an aliphatic backbone to (b) self-emulsifying wax is from 2:3 to 9:1, and
    wherein when the cold process formulation aid is mixed with an aqueous medium at a temperature not exceeding the melt point of the wax component of the cold process formulation aid or the melt point of the cold process formulation aid itself the resulting mixture forms a hydrogel or an emulsion is formed.

16. The anhydrous cold process formulation aid of claim 15 wherein the polymer having an aliphatic backbone is a polyacrylic acid, a polyacrylate, a polyacrylate copolymer, a polyacrylate crosspolymer, or a salt thereof.

17. The anhydrous cold process formulation aid of claim 16 wherein the self-emulsifying wax is a polyglyceryl ester.

18. The anhydrous cold process formulation aid of claim 15 wherein the polymer having an aliphatic backbone is a polyquaternium.

19. The anhydrous cold process formulation aid of claim 18 wherein the self-emulsifying wax is a polyglyceryl ester.

20. An anhydrous cold process formulation aid that does not include a petroleum-based solvent and consists essentially of:
   (i) a polymer having an aliphatic backbone selected from a polyquaternium polymer and a polymer having plurality of pendant groups selected from alkali metal carboxylate groups and ammonium carboxylate groups;
   (ii) a self-emulsifying wax, and
   (iii) a cosmetically-acceptable ester or a Caprylic/Capric Triglyceride wherein when the cold process wax is mixed with an aqueous medium at a temperature not exceeding the melt point of the wax or the melt point of the cold process formulation aid hydrogel or an emulsion is formed.

21. The anhydrous cold process formulation aid of claim 20 wherein the ratio of (a) the polymer having an aliphatic backbone to (b) the self-emulsifying wax to (c) the cosmetically-acceptable ester or Caprylic/Capric Triglyceride is from about 5:30:65 to about 70:15:15.

22. The anhydrous cold process formulation aid of claim 21 wherein the ratio of (a) the polymer having an aliphatic backbone to (b) the self-emulsifying wax to (c) the cosmetically-acceptable ester or Caprylic/Capric Triglyceride is about 60:10:30.

23. The anhydrous cold process formulation aid of claim 20 wherein the polymer having an aliphatic backbone is a polyacrylic acid, a polyacrylate, a polyacrylate copolymer, a polyacrylate crosspolymer, or a salt thereof.

24. The anhydrous cold process formulation aid of claim 23 wherein the self-emulsifying wax is a polyglyceryl ester.

25. The anhydrous cold process formulation aid of claim 20 wherein the polymer having an aliphatic backbone is a polyquaternium.

26. The anhydrous cold process formulation aid of claim 25 wherein the self-emulsifying wax is a polyglyceryl ester.

27. An anhydrous cold process formulation aid in the form of a flake, slab, powder, a paste, a semi-solid, or a slurry consisting essentially of (i) a quaternary ammonium polymer and (ii) a wax selected from the group consisting of natural waxes and synthetic waxes, wherein if the wax is not micronized and is not self-emulsifying, the ratio, by weight, of the non-micronized wax to the quaternary ammonium polymer is from about 60:40 to 80:20, and if the wax is a micronized wax or a self-emulsifying wax, the ratio, by weight, of wax to the quaternary ammonium polymer is 70:30 to 98:2, wherein when the cold process formulation aid is mixed with an aqueous medium at a temperature not exceeding the melt point of the or the melt point of the cold process formulation aid a hydrogel or an emulsion is formed.

* * * * *